US 11,406,695 B2

United States Patent
Zhang et al.

(10) Patent No.: US 11,406,695 B2
(45) Date of Patent: Aug. 9, 2022

(54) **RECOMBINANT EXPRESSION OF *CHLAMYDIA* MOMP ANTIGEN**

(71) Applicant: Merck Sharp & Dohme LLC, Rahway, NJ (US)

(72) Inventors: Lan Zhang, Chalfont, PA (US); Zhiyun Wen, Devon, PA (US); Craig T. Przysiecki, Kintnersville, PA (US); Ping Qiu, Cranbury, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 56 days.

(21) Appl. No.: 16/894,968

(22) Filed: Jun. 8, 2020

(65) Prior Publication Data

US 2021/0093703 A1 Apr. 1, 2021

Related U.S. Application Data

(62) Division of application No. 15/527,789, filed as application No. PCT/US2015/060780 on Nov. 16, 2015, now Pat. No. 10,675,339.

(60) Provisional application No. 62/082,889, filed on Nov. 21, 2014.

(51) Int. Cl.
```
C07H 21/02      (2006.01)
C07H 19/00      (2006.01)
C07H 21/00      (2006.01)
A61K 39/118     (2006.01)
A61K 39/02      (2006.01)
C07K 14/295     (2006.01)
A61P 31/04      (2006.01)
C12N 15/70      (2006.01)
A61K 39/00      (2006.01)
```
(52) U.S. Cl.
CPC .............. *A61K 39/02* (2013.01); *A61P 31/04* (2018.01); *C07K 14/295* (2013.01); *C12N 15/70* (2013.01); *A61K 2039/54* (2013.01); *A61K 2039/55511* (2013.01)

(58) Field of Classification Search
CPC .............................. A61K 39/02; C07K 14/295
See application file for complete search history.

(56) References Cited

U.S. PATENT DOCUMENTS

| | | | |
|---|---|---|---|
| 8,541,007 B2 * | 9/2013 | Alderson | A61K 39/118 424/263.1 |
| 2002/0136742 A1 | 9/2002 | Kousoulas et al. | |
| 2009/0022755 A1 * | 1/2009 | Barth | A61P 33/02 424/190.1 |
| 2009/0214582 A1 | 8/2009 | Dean | |
| 2010/0172927 A1 * | 7/2010 | Alderson | A61P 27/00 424/190.1 |
| 2011/0300206 A1 * | 12/2011 | Alderson | A61K 39/118 424/450 |
| 2014/0056967 A1 * | 2/2014 | Barth | C07K 14/295 424/450 |

FOREIGN PATENT DOCUMENTS

| | | |
|---|---|---|
| EP | 0192033 A2 | 8/1986 |
| WO | 2008040757 A1 | 4/2008 |

OTHER PUBLICATIONS

Zheng et al., Biochem. Cell Biol., 2007; 85: 218-226 (Year: 2007).*
Brunelle et al., Infection and Immunity, 2006; 74(1): 578-585 (Year: 2006).*
Srinivasan et al., Journal of Bacteriology, 2011; 194(3):617-626 (Year: 2011).*
Jeffrey et al., Infection and Immunity, 2010; 78(6):2544-2553 (Year: 2010).*
Baehr, Wolfgang, et al., Mapping antigenic domains expressed by Chlamydia trachomatic major outer membrane protein genes, Proc. Natl. Acad. Sci. USA, 1988, 4000, 85(11).
Biocompare, 2010; Co-expression with pETDuet-1 from Novagen; https://www.biocompare.com/Product-Review/40993-Co-expression-with-pETDuet-1-Duet-Expression-System-From-Novagen/ (Year: 2010).
Brunham, Robert C. et al., Immunology of Chlamydia Infection: Implications for a Chlamydia Trachomatis Vaccine, Nature Reviews Immunology, 2005, 149-161, 5.
Cambridge, Chino D. et al., Formulation, characterization, and expression of a recombinant MOMP Chlamydia trachomatic DNA vaccine encapsulated in chitosan nanoparticles, Int. J. Nanomedicine, 2013, 1759-1771, 8.

(Continued)

*Primary Examiner* — Gary B Nickol
*Assistant Examiner* — Lakia J Jackson-Tongue
(74) *Attorney, Agent, or Firm* — Nichole M. Valeyko; Alysia Finnegan

(57) ABSTRACT

The present invention relates to methods for the recombinant expression of *chlamydia* major outer membrane protein (MOMP) comprising transforming a population of *E. coli* host cells with an expression vector comprising a nucleic acid molecule that encodes *chlamydia* MOMP and encodes a leader sequence for targeting the MOMP to the outer membrane of the cell, wherein the nucleic acid molecule is operatively linked to a promoter. The method of the invention allows expression of MOMP in the outer membrane of the cell, which leads to protein folding that is more like native MOMP relative to a MOMP protein that is expressed intracellularly. Also provided by the invention are uses of the recombinant MOMP in pharmaceutical compositions and methods for the treatment and/or prophylaxis of *chlamydia* infection and/or the effects thereof.

Figure 1:
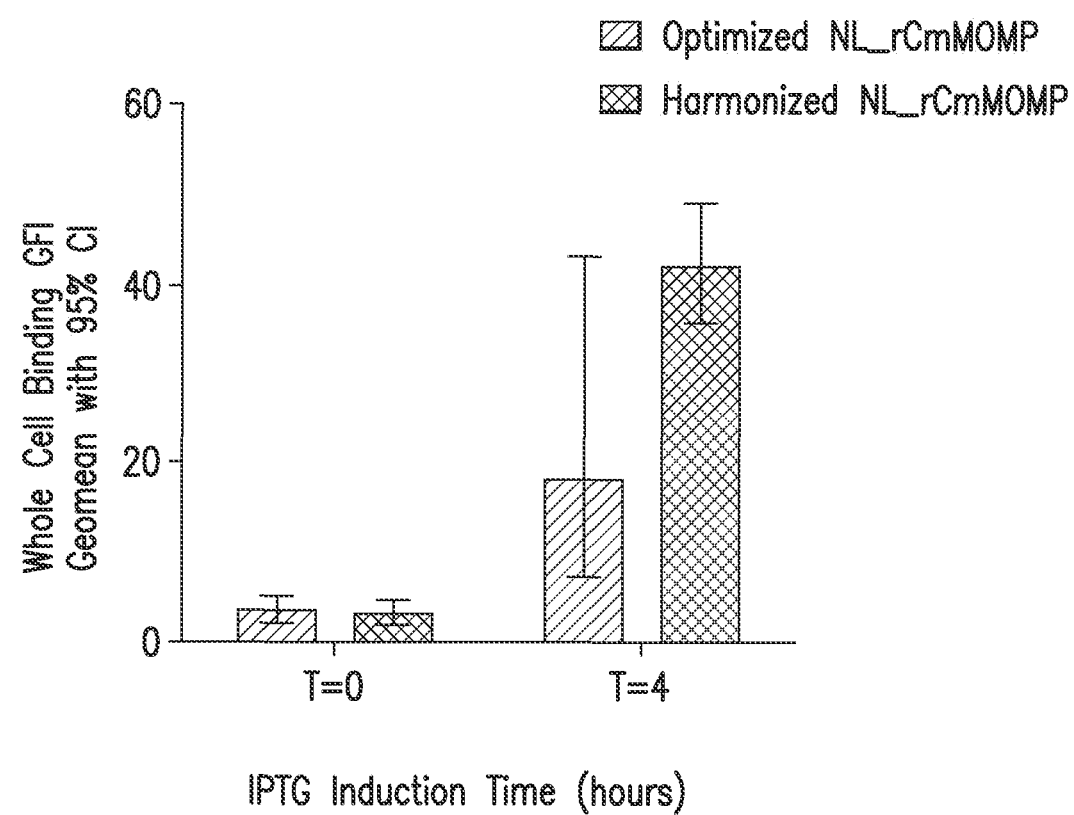
Figure 2A:
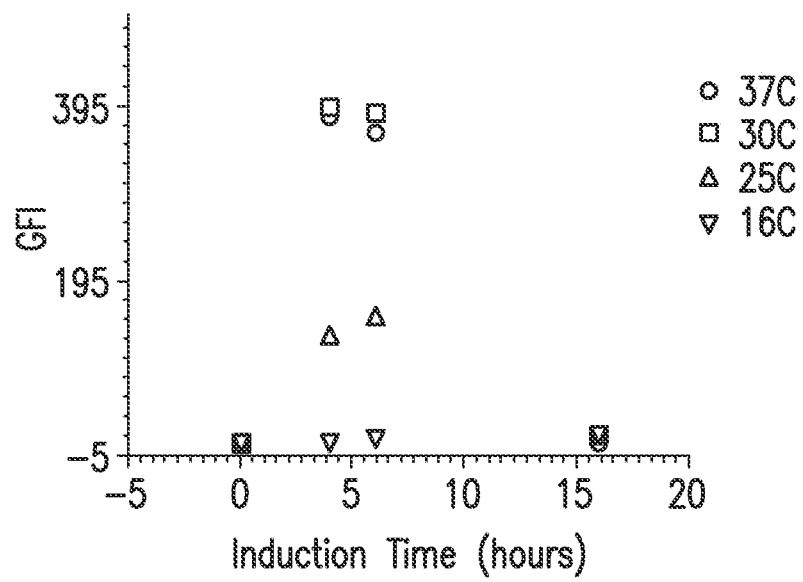
Figure 2B:
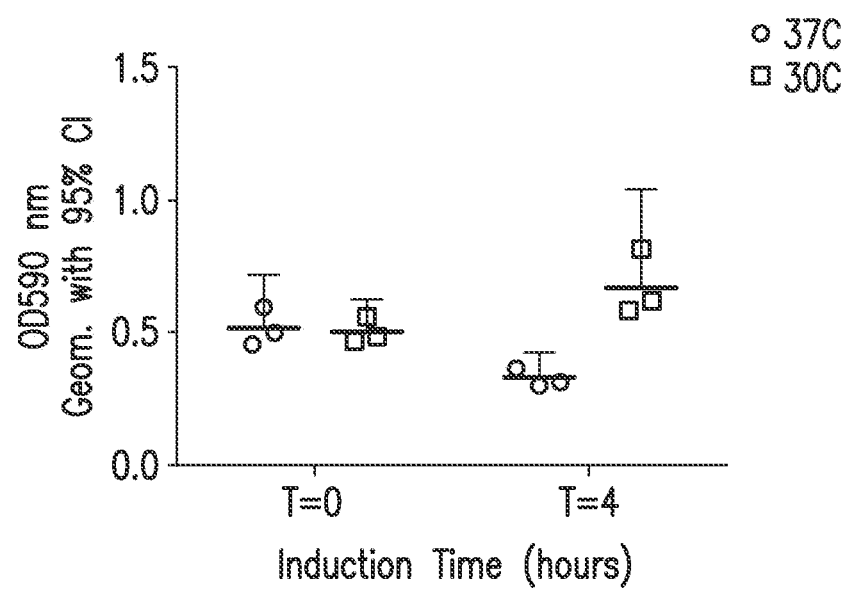
Figure 2C:
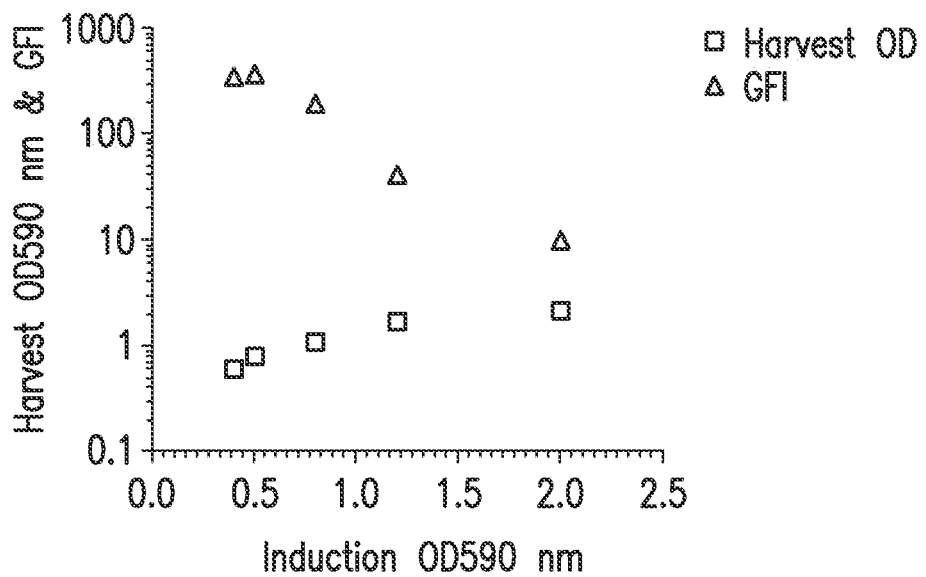
Figure 2D:
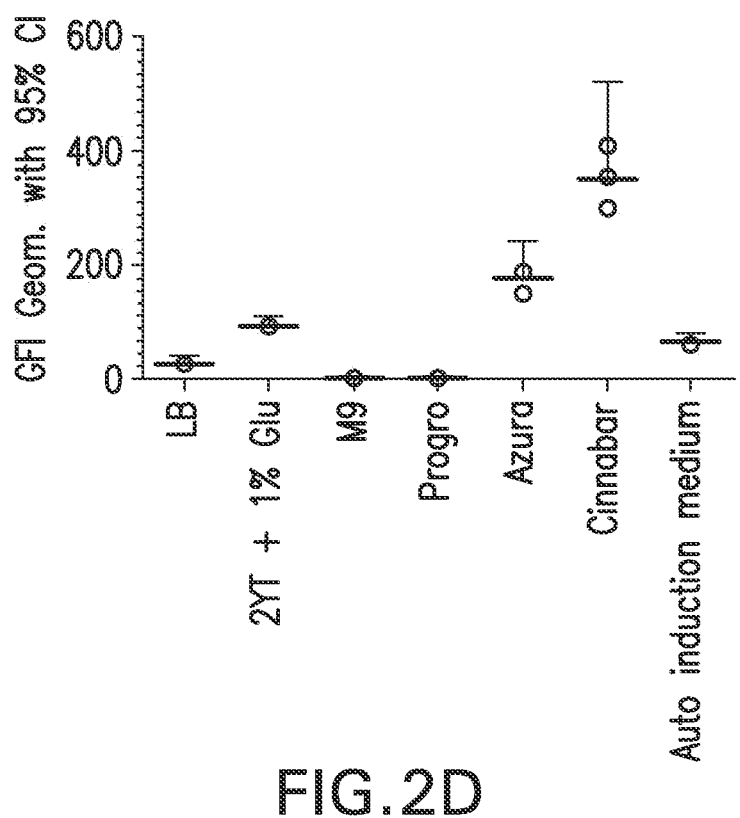
Figures 3A, 3B:
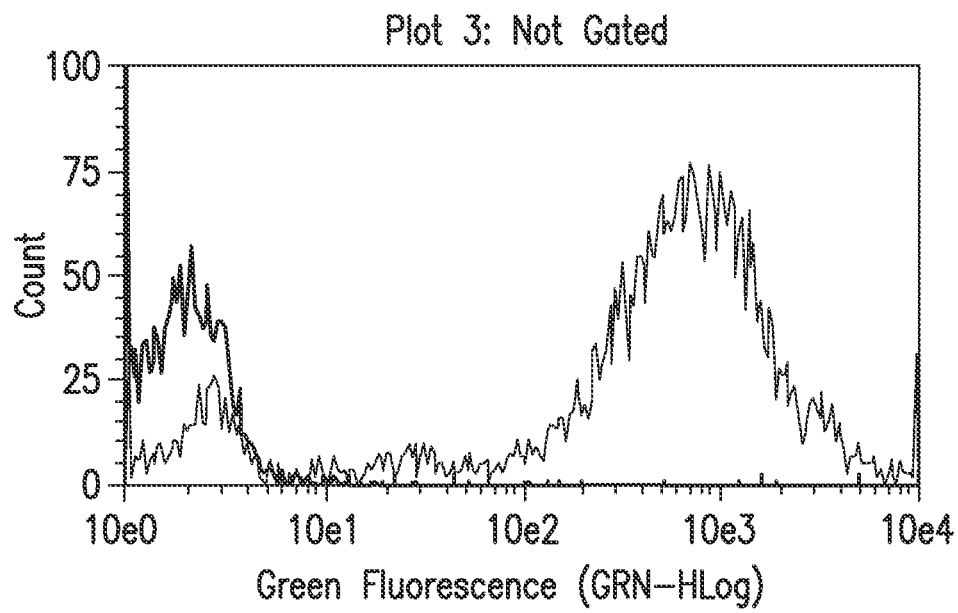
Figure 4B:
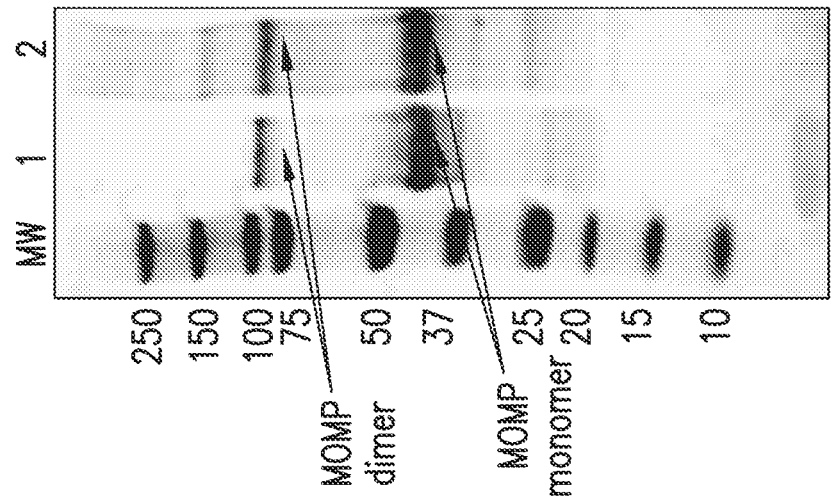
Figure 4A:
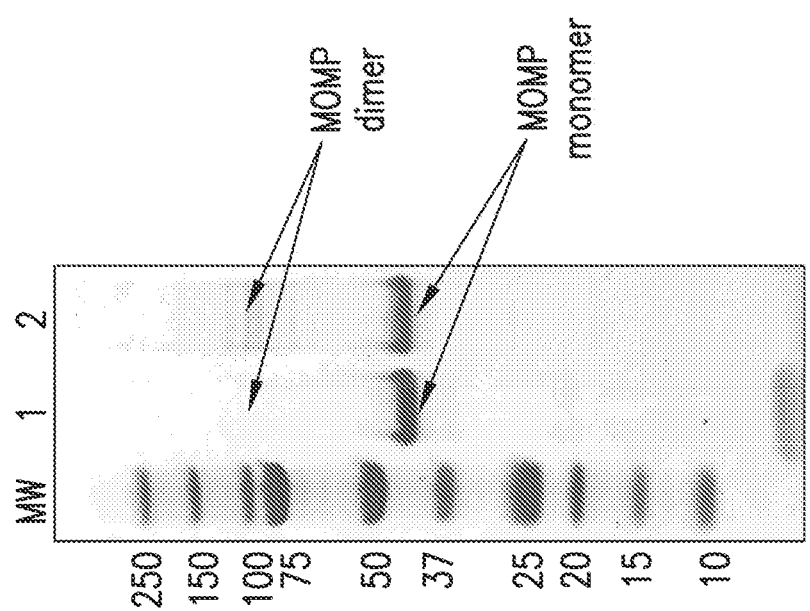
Figure 4D:
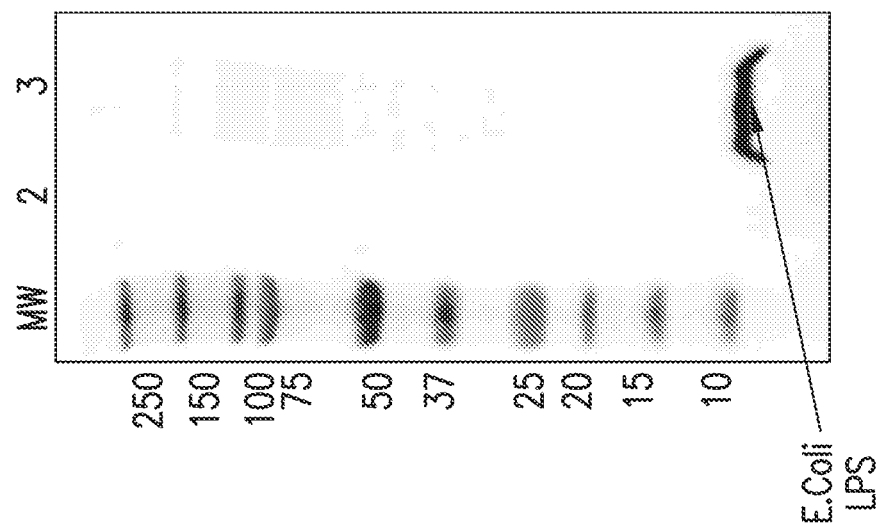
Figure 4C:
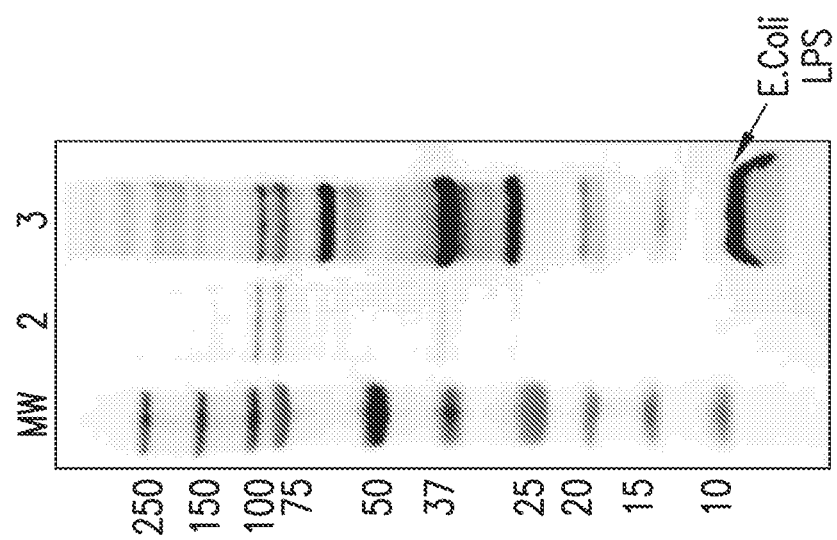
Figure 6:
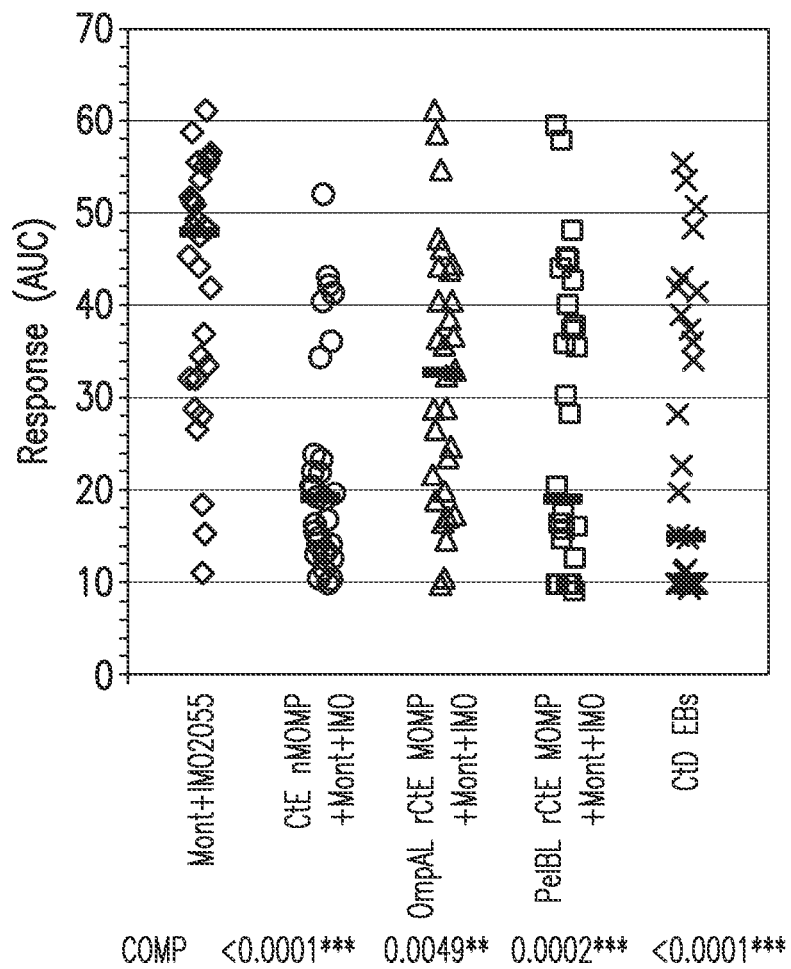

9 Claims, 8 Drawing Sheets
Specification includes a Sequence Listing.

(56) References Cited

OTHER PUBLICATIONS

EMBL—Protein Expression and Purification Core Facility; Protein Expression and *E. coli*; accessed on Jun. 4, 2019; https://www.embl.de/pepcore/pepcore_services/protein_expression/ecoli/ (Year: 2019).

Evelina Angov, Heterologous Protein Expression is Enhanced by Harmonizing the Codon Usage Frequencies of the Target Gene with those of the Expression Host, PlosOne, 2008, 1-10, 3(5).

Farris, Christina M. et al., Vaccination against Chlamydia Genital Infection utilizing the Murine C. muridarum Model, Infection and Immunity, 2011, 986-996, 79(3).

Harlan D. Caldwell et al., Purification and Partial Characterization of the Major Outer Membrane Protein of Chlamydia trachomatic, Infection and Immunity, 1988, 1161-1176-, 31(3).

Heather E. Findlay, Surface expression, single-channel analysis and membrane topology of recombinant Chlamydia trachomatic Major Outer Membrane Protein, BMC Microbiology, 2005, 1-15, 5(5).

Hickey, Danica K. et al., Intranasal immunization with C. muridarum major outer membrane protein (MOMP) and cholera toxin elicits local production of neutralising IgA in the prostate, Vaccine, 2004, 4306-4315, 22.

Kalbina, Irina et al., A novel chimeric MOMP antigen expressed in *Escherichia coli, Arabidopsis thaliana*, and Daucus carota as a potential Chlamydia trachomatic vaccine candidate, Protein Expression and Purification, 2011, 194-202, 80.
Menart, Viktor, Constitutive Versus Thermoinducible Expression of Heterologous Proteins in *Escherichia coli* Based on Strong PR, PL Promoters from Phage Lambda, Biotechnology and Bioengineering, 2003, 181-190, 83(2).
O'Meara, Connor P. et al., Immunization with a MOMP-Based Vaccine Protects Mice against a Pulmonary Chlamydia Challenge and Identifies a Disconnection between Infection and Pathology, PLOS One, 2013, 1-14, 8(4).
Skelding, Kathryn A. et al., Comparison of intranasal and transcutaneous immunizaiton for induction of protective immunity against Chlamydia muridarum respiratory tract infection, Vaccine, 2006, 355-366, 24.
T.A. Thanaraj, Protein secondary structural types are differentially coded on messenger RNA, Protein Science, 1996, 1973-1983, 5.
Tifrea, Delia F. et al., Vaccination with the Recombinant Major Outer Membrane Protein Elicits Antibodies to the Constant Domains and Induces Cross-Serovar Protection against Intransal Challenge with Chlamydia trachomatic, Infection and Immunity, 2013, 1741-1750, 81(5).
Jose Montoya, Wilson, Walter et al., Chlamydia, Current Diagnosis & Treatment in Infectious Diseases, 2001, 694-702, 1.
Zhao, et al., GenBank_AV732495 AY732495.1 Synthetic construct mutated McPn-MOMP gene, complete cds, GenBank Nuclotide NCBI, 2004, 1, 1.

* cited by examiner

| Geomean Fluorescence intensity | Anti-CtE EB mouse sera | Negative Control |
|---|---|---|
| T=0h | 3 | 3 |
| T=4h (induced) | 299 | 2 |

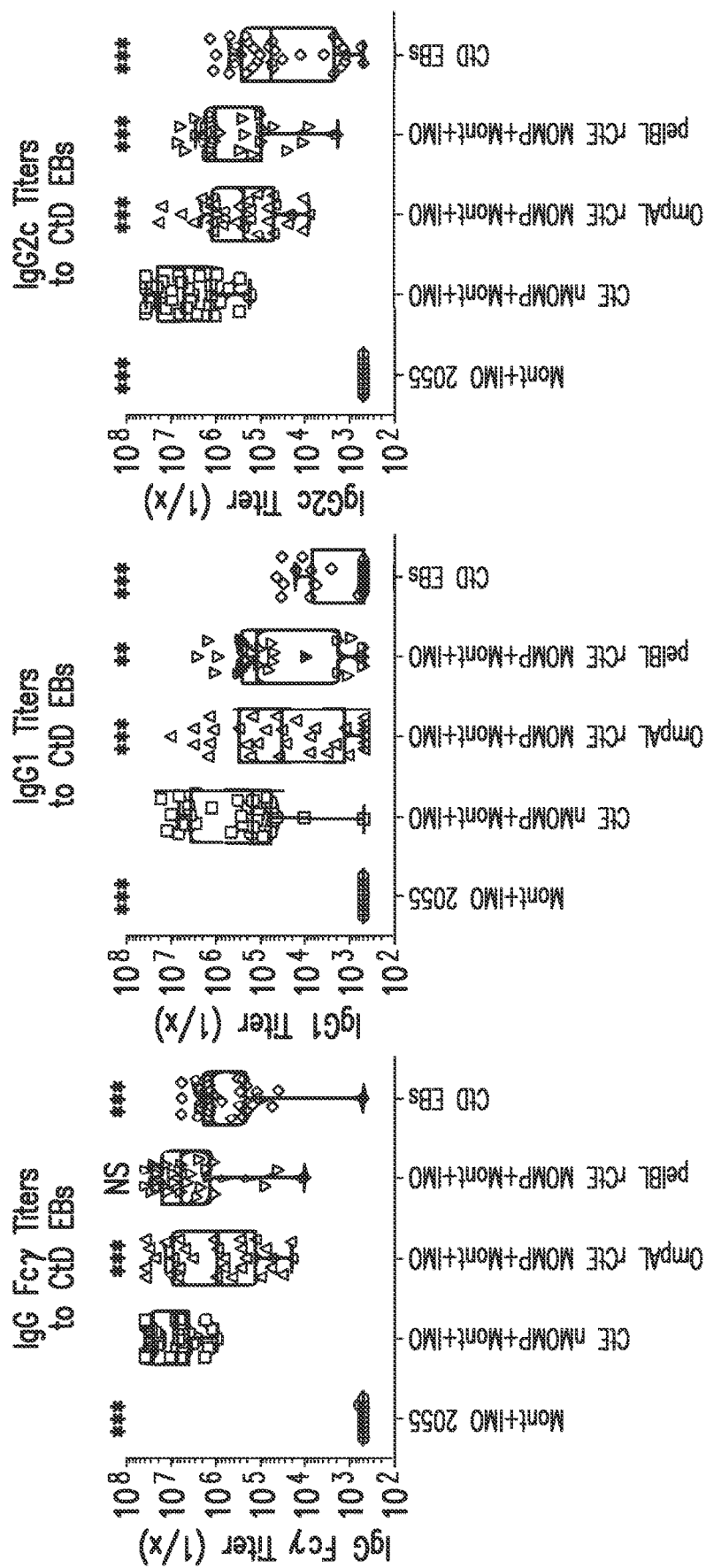

RECOMBINANT EXPRESSION OF *CHLAMYDIA* MOMP ANTIGEN

CROSS-REFERENCE TO RELATED APPLICATIONS

This application is a divisional application of U.S. application Ser. No. 15/527,789, filed May 18, 2017, which is a § 371 National Phase Application of International Application No. PCT/US15/060780, filed Nov. 16, 2015, which claims the benefit of U.S. provisional application No. 62/082,889, filed Nov. 21, 2014, the contents of which are hereby incorporated by reference in their entirety.

FIELD OF THE INVENTION

The present invention relates to methods for the recombinant expression of *Chlamydia* antigen MOMP and translocation to the outer membrane of *E. coli*, pharmaceutical compositions comprising recombinant MOMP and uses of the recombinant MOMP and pharmaceutical compositions of the invention in methods for the prevention of *Chlamydia* infection and/or the clinical manifestations thereof.

REFERENCE TO SEQUENCE LISTING SUBMITTED ELECTRONICALLY

The sequence listing of the present application is submitted electronically via EFS-Web as an ASCII formatted sequence listing with a file name "23870USDIV-SEQLIST.TXT", creation date of Jun. 4, 2020, and a size of 53 kB. This sequence listing submitted via EFS-Web is part of the specification and is herein incorporated by reference in its entirety.

BACKGROUND OF THE INVENTION

*Chlamydia trachomatis* is an obligate intracellular Gram-negative bacterium responsible for a number of pathologies, including ocular trachoma and several sexually transmitted diseases. There are many different strains of *C. trachomatis*, which are separated into multiple serovars based on serological differences in the chlamydial major outer membrane protein (MOMP). *C. trachomatis* serovars A, B, Ba, and C are responsible for ocular trachoma which can cause conjunctivitis, conjunctival scarring and corneal scarring. *C. trachomatis* serovars D, Da, E, F, G, H, I, Ia, J, Ja and K are responsible for oculogenital disease which can cause cervicitis, urethritis, endometritis, pelvic inflammatory disease, tubal infertility, ectopic pregnancy, neonatal conjunctivitis and infant pneumonia. *Chlamydia trachomatis* serovars L1, L2 and L3 are responsible for lymphogranuloma venereum, which can cause submocosa and lymph-node invasion, with necrotizing granulomas and fibrosis. (Reviewed in Brunham et al., *Nature Reviews Immunology* 5:149-161, 2005; Montoya, *Chlamydia*, p. 694-702, In Wilson et al., Eds. *Current Diagnosis & Treatment in Infectious Diseases*, The McGraw-Hill Companies, Inc. 2001.) Asymptomatic genital *Chlamydia* infections are also common, which may lead to infertility in women that are left untreated.

*Chlamydia trachomatis* infects mucosal epithelial cells. Like other *Chlamydia*, *C. trachomatis* undergoes a biphasic development cycle in which it begins the cycle as a metabolically inactive infectious elementary body (EB) and transforms into a metabolically active reticulate body (RB). The bacterium exists outside the host cell as an EB, which is internalized by a host cell and surrounded by an endosomal membrane forming an inclusion body, where the EB transforms into a metabolically active RB. The RB can divide by binary fusion. Within about 40-48 hours, the RB transforms back to an EB, which is released by the host cell and can infect neighboring cells. (Id.)

*Chlamydia* MOMPs are part of a larger family of genetically related outer membrane proteins (the OmpA family) that are heat-modifiable, surface exposed porin proteins. OmpA proteins have a structurally similar N-terminal domain that is embedded in the bacterial outer membrane. OmpA proteins have been targeted for vaccine development because of their surface exposure, high immunogenicity, and role in the interaction between the bacteria and their host cells. Specifically, *Chlamydia* MOMP has been a vaccine target for many researchers (Cambridge et al., *Int. J. Nanomedicine* 8:1759-71 (2013); Farris et al., *Infection and Immunity* 79(3): 986-996 (2011); Hickey et al., *Vaccine* 22:4306-4315 (2004); Kalbina et al., *Protein Expression and Purification* 80: 194-202 (2011); O'Meara et al., *PLOS One* 8(4): 1-14; Skelding et al., *Vaccine* 24:355-366 (2006), Tifrea et al., *Infection and Immunity* 81(5): 1741-1750 (2013)). However, a safe and effective *Chlamydia* vaccine remains unavailable to reduce the risk of *Chlamydia* infection or its associated pathogenic effects. Additional vaccine candidates and methods for making them are therefore needed.

SUMMARY OF THE INVENTION

The present invention is related to a method for the recombinant expression of *Chlamydia* major outer membrane protein (MOMP) comprising: (a) transforming a population of *E. coli* host cells with an expression vector comprising a nucleic acid molecule comprising a sequence of nucleotides that encode a leader sequence for targeting the MOMP to the outer membrane of the cell and a sequence of nucleotides that encode *Chlamydia* MOMP, wherein the nucleic acid molecule is operatively linked to a promoter; (b) culturing the transformed cells under conditions that permit expression of the nucleic acid molecule and translocation to the outer membrane of the cells to produce a recombinant *Chlamydia* MOMP; and (c) optionally purifying the MOMP. The method of the invention allows recombinant expression of MOMP in the outer membrane of the cell, which leads to protein folding that is more like native MOMP relative to a recombinant MOMP protein that is expressed intracellularly.

In some embodiments of the invention, the nucleotide sequence encoding MOMP and/or the nucleotide sequence encoding the leader sequence is codon harmonized. In alternative embodiments, the nucleotide sequence encoding MOMP and/or the nucleotide sequence encoding the leader sequence is codon optimized.

In some embodiments of the invention, the leader sequence comprises the *Shigella flexneri* SopA sequence, the *Salmonella enterica* PgtE sequence, the *Yersinia pestis* Pla, the *E. coli* OmpP sequence, the *E. coli* OmpA sequence, or the pectate lysase B (PelB) sequence.

In further embodiments, expression of the recombinant MOMP is optimized by using a low or moderate strength promoter. In additional embodiments, optimized expression is achieved through using a vector that is characterized by a transcription/translation rate that is constrainable to low or moderate.

Also provided herein are recombinant MOMPs produced by the methods of the invention and pharmaceutical compositions comprising an effective amount of a recombinant MOMP of the invention and a pharmaceutically acceptable carrier.

In a further aspect, the invention provides methods for the treatment or prophylaxis of *Chlamydia* in a patient by administering a recombinant MOMP or a pharmaceutical composition of the invention to the patient.

As used throughout the specification and in the appended claims, the singular forms "a," "an," and "the" include the plural reference unless the context clearly dictates otherwise.

As used throughout the specification and appended claims, the following definitions and abbreviations apply:

As used herein, the term "recombinant" refers to a polypeptide or nucleic acid that does not exist in nature. The term "recombinant" polypeptide refers to a polypeptide that is prepared, expressed, created, or isolated by recombinant means, such as polypeptides expressed using a recombinant expression vector transfected into a host cell. A recombinant polynucleotide mal also include two or more nucleotide sequences artificially combined and present together in a longer polynucleotide sequence, wherein the two sequences are not found together (e.g. attached or fused) in nature, e.g. a promoter and a heterologous nucleotide sequence encoding a polypeptide that are normally not found together in nature or a vector and a heterologous nucleotide sequence.

As used herein, the terms "isolated" or "purified" refer to a molecule (e.g., nucleic acid, polypeptide, bacterial strain, etc.) that is at least partially separated from other molecules normally associated with it in its native state. An "isolated or purified polypeptide" is substantially free of other biological molecules naturally associated with the polypeptide such as nucleic acids, proteins, lipids, carbohydrates, cellular debris and growth media. An "isolated or purified nucleic acid" is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. Generally, the terms "isolated" and "purified" are not intended to refer to a complete absence of such material or to an absence of water, buffers, or salts, unless they are present in amounts that substantially interfere with experimental or therapeutic use of the molecule.

As used herein, "homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms that are often used for sequence analysis: BLAST ALGORITHMS: Altschul, S. F., et al., (1990) J. Mol. Biol. 215: 403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

The term "cassette" refers to a nucleic acid molecule which comprises at least one nucleic acid sequence that is to be expressed, along with its transcription and translational control sequences. Changing the cassette, will cause the vector into which is incorporated to direct the expression of different sequence or combination of sequences. In the context of the present invention, the nucleic acid sequences present in the cassette will usually encode any polypeptide of interest such as an immunogen. Because of the restriction sites engineered to be present at the 5' and 3' ends, the cassette can be easily inserted, removed or replaced with another cassette.

The term "promoter" refers to a recognition site on a DNA strand to which an RNA polymerase binds. The promoter forms an initiation complex with RNA polymerase to initiate and drive transcriptional activity. The complex can be modified by activating sequences such as enhancers, or inhibiting sequences such as silencers.

"MAA" means an amorphous aluminum hydroxyphosphate sulfate adjuvant.

As used herein, an "ISCOM-type adjuvant" is an adjuvant comprising an immune stimulating complex (ISCOM), which is comprised of a saponin, cholesterol, and a phospholipid, which together form a characteristic caged-like particle, having a unique spherical, caged-like structure that contributes to its function (for review, see Barr and Mitchell, *Immunology and Cell Biology* 74: 8-25 (1996)). This term includes both ISCOM adjuvants, which are produced with an antigen and comprise antigen within the ISCOM particle and ISCOM matrix adjuvants, which are hollow ISCOM-type adjuvants that are produced without antigen.

As used herein, the term "derivative" refers to a polypeptide having one or more alterations, which can be changes in the amino acid sequence (including additions and deletions of amino acid residues) and/or chemical modifications, relative to a reference sequence (e.g., a leader sequence and/or MOMP sequence described herein). In preferred embodiments, the derivative is at least 85%, at least 90%, at least 95%, at least 97%, at least 99% identical to the original reference sequence prior to alteration. In general, derivatives retain the activity of the reference sequence, e.g. inducing an immune response. As used herein, the term "derivative" is not limited to derivatives of a wild-type or native reference sequence, but includes derivatives of a mutant sequence as a reference sequence. In preferred embodiments, any specified mutations of the mutant reference sequence are maintained, but alterations/modifications relative to the mutant reference sequence are included in the derivative sequence at amino acid residues other than the specified mutations of the reference sequence. As used herein, the term "derivative" also includes polynucleotides that have one or more alterations relative to a reference nucleotide sequence.

In one embodiment, a derivative is a polypeptide that has an amino acid sequence which differs from the base sequence from which it is derived by one or more amino acid substitutions. Amino acid substitutions may be "conservative" (i.e. the amino is replaced with a different amino acid from the same class of amino acids (e.g., non-polar, polar/neutral, acidic and basic), an amino acid with broadly similar properties, or with similar structure (aliphatic, hydroxyl or sulfur-containing, cyclic, aromatic, basic, and acidic)) or "non-conservative" (i.e. the amino acid is replaced with an amino acid of a different type). Broadly speaking, fewer non-conservative substitutions will be possible without altering the biological activity of the polypeptide. Some embodiments of the invention include derivatives that include substitution of no more than 25 amino acid residues, 20 amino acid residues, 15 amino acid residues, 12 amino acid residues, 11 amino acid residues, 10 amino acid residues, 9 amino acid residues, 8 amino acid residues, 7 amino acid residues, 6 amino acid residues, 5 amino acid residues, 4 amino acid residues, 3 amino acid residues, 2 amino acid residues, or 1 amino acid residue that is/are substituted relative to a reference sequence.

In another embodiment, a derivative is a polypeptide that has an amino acid sequence which differs from the base sequence from which it is derived by having one or more amino acid deletions and/or additions in any combination. Deleted or added amino acids can be either contiguous or individual residues. In some embodiments, no more than 25 amino acid residues, no more than 20 amino acid residues, no more than 15 amino acid residues, no more than 12 amino acid residues, no more than 10 amino acid residues, no more than 8 amino acid residues, no more than 7 amino acid residues, no more than 6 amino acid residues, no more than 5 amino acid residues, no more than 4 amino acid residues, no more than 3 amino acid residues, no more than 2 amino acid residues, or no more than 1 amino acid residue is/are deleted or added relative to a reference sequence.

In another embodiment, a derivative is a polypeptide that has an amino acid sequence which differs from the base sequence from which it is derived by having one or more chemical modifications of the protein. Chemical modifications include, but are not limited to, modification of functional groups (such as alkylation, hydroxylation, phosphorylation, thiolation, carboxylation and the like), incorporation of unnatural amino acids and/or their derivatives during protein synthesis and the use of crosslinkers and other methods which impose conformational constraints on the polypeptides.

As used herein, the term "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering or substantially altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

The term "treatment" refers to both therapeutic treatment and prophylactic or preventative measures. Individuals "in need of" treatment include those already with a *Chlamydia* infection, whether or not manifesting any clinical symptoms, as well as those at risk of being infected with *Chlamydia*. Treatment of a patient with the pharmaceutical compositions of the invention includes one or more of the following: inducing/increasing an immune response against *Chlamydia* in the patient, inducing/increasing a virus neutralizing antibody response against one or more *Chlamydia* viruses, preventing, ameliorating, abrogating, or reducing the likelihood of the clinical manifestations of *Chlamydia* in patients who have been infected with *Chlamydia*, preventing or reducing the likelihood of developing oculogenital disease, cervicitis, urethritis, endometritis, pelvic inflammatory disease, tubal infertility, ectopic pregnancy, neonatal conjunctivitis, infant pneumonia and/or other disease or complication associated with *Chlamydia* infection, reducing the severity or duration of the clinical symptoms of *Chlamydia* infection and/or other disease or complication associated with *Chlamydia*, and preventing or reducing the likelihood of *Chlamydia* infection.

The term "therapeutically effective amount" or "effective amount" means sufficient pharmaceutical composition comprising recombinant MOMP is introduced to a patient to produce a desired effect, including, but not limited to: inducing/increasing an immune response against *Chlamydia* in the patient, inducing/increasing a neutralizing antibody response against *Chlamydia* in a patient, preventing or reducing the likelihood of *Chlamydia* infection, preventing or reducing the likelihood of *Chlamydia* recurrent infection, preventing, ameliorating or abrogating the clinical manifestations of *Chlamydia* infection in patients who have been infected with *Chlamydia*, preventing one or more of ocular trachoma, conjunctivitis, conjunctival scarring, corneal scarring, oculogenital disease, cervicitis, urethritis, endometritis, pelvic inflammatory disease, tubal infertility, ectopic pregnancy, neonatal conjunctivitis, infant pneumonia, and lymphogranuloma venereum; reducing the severity or duration of disease associated with *Chlamydia*. One skilled in the art recognizes that this level may vary.

"An immunologically effective amount" refers to the amount of an immunogen that can induce an immune response against the heterologous polypeptide when administered to a patient that can protect the patient from infection by the pathogen that expresses the heterologous polypeptide (including primary, recurrent and/or super-infections) and/or ameliorate at least one pathology associated with infection and/or reduce the severity/length of infection in the patient. The amount is sufficient to significantly reduce the likelihood or severity of an infection. Animal models known in the art can be used to assess the protective effect of administration of immunogen. For example, immune sera or immune T cells from individuals administered the immunogen can be assayed for neutralizing capacity by antibodies or cytotoxic T cells or cytokine producing capacity by immune T cells. The assays commonly used for such evaluations include but not limited to viral neutralization assay, anti-viral antigen ELISA, interferon-gamma cytokine ELISA, interferon-gamma (IFN-γ) ELISPOT, intracellular multi-cytokine staining (ICS), and $^{51}$Chromium release cytotoxicity assay. Animal challenge models can also be used to determine an immunologically effective amount of immunogen.

The term "immune response" refers to a cell-mediated (T-cell) immune response and/or an antibody (B-cell) response.

The term "patient" refers to any human being that is to receive the pharmaceutical compositions described herein, including both immunocompetent and immunocompromised individuals. As defined herein, a "patient" includes those already infected with *Chlamydia*, either through natural infection or vaccination or those that may subsequently be exposed.

Additional abbreviations employed herein include the following: CI is confidence interval; Cm is *Chlamydia muridarium*; CtD is *Chlamydia trachomatis* Serovar D, CtE is *Chlamydia trachomatis* Serovar E, FACS is fluorescent activated cell sorting; GFI is geometric mean fluorescence intensity; IPTG is isopropyl β-D-1-thiogalactopyranoside; LPS is lipopolysaccharide MOMP is major outer membrane protein; rMOMP is recombinant MOMP; rCmMOMP is recombinant *Chlamydia muridarium* MOMP; nOMV is a native outer membrane vesicle from *E. coli* that does not contain a recombinant MOMP gene and OM is outer membrane.

BRIEF DESCRIPTION OF THE DRAWINGS

FIG. 1 shows the effect of codon usage harmonization on rMOMP surface expression level. FACS geometric mean (geomean) fluorescence intensity (GFI) is shown for harmonized or optimized rCmMOMP genes at T=0 and T=4 hours after IPTG induction. Geometric means of GFI from three independent experiments were plotted with 95% confidence interval.

FIGS. 2 A-D provide an evaluation of expression conditions for rCtE MOMP with a PelB leader sequence, which was constructed in the pAVE029 vector. FIG. 2A shows the surface expression (FACS GFI) of rCtE MOMP after different IPTG induction times (T=0 and T=4 hours) when expressed at different temperatures (37° C.=circles, 30° C.=squares, 25° C.=triangles, 16° C.=downward pointing triangles). FIG. 2B shows the cell concentration (OD590, geomean, 95% CI) at different temperatures (37° C.=circles, 30° C.=squares) after T=0 and T=4 IPTG induction time and indicates the cell fragility. FIG. 2C shows the surface expression with different cell densities at induction (T=0). FIG. 2D shows the surface expression (FACS GFI, geomean, 95% CI) with different cell culture media.

FIGS. 3A and 3B show expression of rCtE-MOMP on *E. coli* outer membrane under optimized expression conditions. An *E. coli* transformant expressing rCtE-MOMP with a PelB leader constructed in a pAVE029 vector was grown in Cinnabar medium at 37° C. and induced by 1 mM IPTG at 30° C. for 4 hours when OD590 reaches ~0.5. FIG. 3A shows a whole cell flow cytometry binding histogram using anti-CtE EB mouse sera and a negative control antibody at the end of induction. The geomean fluorescence intensity is provided in FIG. 3B.

FIGS. 4A-D show expression of purified rCtE-MOMP. (FIG. 4A) SDS-PAGE; (FIG. 4B) anti-CtE EB mouse sera western blot; (FIG. 4C) anti-*E. coli* control nOMV (native outer membrane vesicle from *E. coli* that does not contain recombinant MOMP gene) mouse sera; (D) anti-*E. coli* LPS monoclonal antibody. Sample 1, control nMOMP; sample 2, purified rMOMP; sample 3, *E. coli* whole cell lysate; all samples are heated and reduced. Monomeric and dimeric forms of MOMP are indicated.

FIGS. 5A-C shows serum antibody responses against CtD EB in immunized mice: (FIG. 5A) IgG Fcγ antibody titers; (FIG. 5B) IgG1 antibody titers; (FIG. 5C) IgG2c antibody titers. Raw data were plotted on Log 10 scale with Box and Whisker Plots (Tukey), boxes=medians with interquartile (IQR) ranges, whiskers=1.5 times the IQR distances. Transformed data were analyzed by One-way ANOVA with Dunnett post test (compared to G2: CtE nMOMP+Mont+IMO2055), * p<0.05,  p<0.01, * p<0.001, NS not significant.

FIG. 6 provides results of a murine challenge study. Individual AUC values were calculated from qPCR and scatter plotted for each group. Black bar, group median. Data were analyzed by One-way ANOVA (compared to G1:

Mont+IMO2055 adjuvant control), * p<0.05,  p<0.01, * p<0.001, NS not significant.

DETAILED DESCRIPTION OF THE INVENTION

*Chlamydia* major outer membrane protein (MOMP) is a target for vaccine development to reduce the risk of *Chlamydia* infection or its associated clinical manifestations due to its surface exposure and high immunogenicity. Native MOMP can be purified from an infected cell line, but development of a robust, cost-effective commercial manufacturing process based on the use of native MOMP can be challenging. Recombinant expression of vaccine antigens is an alternative method to purification of native antigen, which may be easier to scale-up to a commercial manufacturing level. However, previous attempts to recombinantly express *Chlamydia* MOMP intracellularly have resulted in insoluble MOMP protein, which is not useful as a vaccine antigen.

To that end, one aspect of the invention provides a method for the recombinant expression of *Chlamydia* MOMP wherein the MOMP protein is recombinantly expressed and translocated to the outer membrane of an *E. coli* cell. Without wishing to be bound by theory, it is thought that expression of MOMP in the outer membrane of *E. coli* results in a MOMP protein that is folded in a manner that more closely resembles native MOMP, which is normally expressed on the cell membrane. Accordingly, the method of the invention comprises: (a) transforming a population of *E. coli* host cells with an expression vector comprising a nucleic acid molecule comprising a sequence of nucleotides that encode a leader sequence for targeting the MOMP to the outer membrane of the cell and a sequence of nucleotides that encode *Chlamydia* MOMP, wherein the nucleic acid molecule is operatively linked to a promoter; (b) culturing the transformed cells under conditions that permit expression of the nucleic acid molecule and translocation to the outer membrane of the cells to produce a recombinant *Chlamydia* MOMP; and (c) optionally purifying the MOMP. The *E. coli* outer membrane expressed recombinant MOMP produced by the method of the invention is shown herein to elicit comparable protection relative to native MOMP in a *Chlamydia* animal challenge model (see Examples 10-13).

Heterologous protein expression systems may produce inadequate expression or formation of insoluble protein aggregates due to differences between the codon usage of the recombinant host cell and the natural cell type. A "triplet" codon of four possible nucleotide bases can exist in over 60 variant forms. Because these codons provide the message for only 20 different amino acids (as well as translation initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon use frequencies for microorganisms has revealed endogenous DNA of *E. coli* most commonly contains the CTG leucine-specifying codon, while the DNA of yeasts and slime molds most commonly includes a TTA leucine-specifying codon. To that end, embodiments of the invention provide methods for the heterologous expression of *Chlamydia* MOMP in the OM of an *E. coli* host cell, wherein the gene sequence encoding the MOMP is either (1) codon harmonized or (2) codon optimized for optimal expression in an *E. coli* host cell.

Thus, in accordance with one aspect of this invention, MOMP-encoding genes were converted to sequences having identical translated sequences but with harmonized codon usage as described by Angov et al. (Heterologous protein expression is enhanced by harmonizing the codon usage frequencies of the target gene with those of the expression host PLOS one 3(5): 1-10 (2008)). Codon harmonization relies on known relationships between secondary protein structure and codon usage frequencies to modulate translation rates at domain boundaries (i.e. link/end segments). The methodology generally consists of identifying slowly translated regions in the wild-type mRNA that are associated with domain boundaries and replacing codons in said region with synonymous codons having usage frequencies in the recombinant host cell that are less than or equal to the usage frequencies of the codons in the native expression host. Id. For regions outside of the domain boundaries, codons are selected that have usage frequencies that are closely matched to the native expression system. Id. It is shown herein that expression of a codon-harmonized DNA sequence encoding *Chlamydia* MOMP results in a higher expression level relative to a codon-optimized DNA sequence encoding the same MOMP polypeptide.

Thus, the invention relates to codon harmonized nucleic acid molecules encoding *Chlamydia* MOMP or a derivative thereof, or encoding *Chlamydia* MOMP plus a leader sequence for targeting the MOMP to the outer membrane of the cell, as discussed, infra. Also provided by the invention are methods for the recombinant expression of *Chlamydia* MOMP, as described in any embodiment herein, wherein the nucleotide sequence encoding MOMP and/or the nucleotide sequence encoding the leader for targeting the MOMP to the OM of the cell are codon harmonized.

In alternative embodiments of the invention, the MOMP-encoding gene is codon-optimized for high levels of expression in the intended host cell, e.g. *E. coli*. The process of codon optimization generally consists of identifying codons in the wild-type sequence that are not commonly associated with highly expressed genes in the intended host cell and replacing them with optimal codons for high expression in the intended host (i.e. codons that are frequently associated with high levels of expression in the recombinant expression host). The new gene sequence is then inspected for undesired sequences generated by these codon replacements (e.g., "ATTTA" sequences, inadvertent creation of intron splice recognition sites, unwanted restriction enzyme sites, high GC content, presence of transcription termination signals that are recognized by yeast, etc.). Undesirable sequences are eliminated by substitution of the existing codons with different codons coding for the same amino acid. The synthetic gene segments are then tested for improved expression.

The methods described above were used to create synthetic genes encoding MOMP, resulting in a gene comprising codons that are harmonized or optimized for improved expression in the intended host, e.g. *E. coli*. While the above procedures provide a summary of the methodology for designing codon harmonized and codon-optimized genes for use in the methods of the invention, it is understood by one skilled in the art that similar expression of genes may be achieved by minor variations in the procedure or by minor variations in the sequence. For example, the procedure for codon optimization, as described herein, may comprise replacement of all of the codons in a given sequence with synonymous codons associated with high levels of expression in the host cell, or comprise replacement of only some of the codons in the wild-type sequence, for example, 20%, 25%, 30%, 40%, 50%, 60%, 70%, 80%, 90%, 95% or more of the wild-type codons can be replaced. For example, in some instances, codons in the wild-type sequence may naturally match that of the preferred codon in the intended host cell and a replacement with a synonymous codon may not be necessary and/or desired.

As discussed, supra, the methods of the invention utilize an expression vector comprising a nucleic acid molecule comprising a sequence of nucleotides that encode a leader sequence for targeting the MOMP to the outer membrane of the cell and a sequence of nucleotides that encode *Chlamydia* MOMP, wherein the nucleic acid molecule is operatively linked to a promoter. In embodiments of the invention, the leader sequence is operatively linked to the N-terminus (i.e. amino or NH$_2$ terminus) of the MOMP. In preferred embodiments, the leader sequence is directly adjacent to the MOMP sequence. In alternative embodiments, additional amino acid residues may be present between the leader and the MOMP, e.g. a single amino acid residue, two amino acid residues, three amino acid residues, four amino acid residues, or five or more amino acid residues. In embodiments wherein additional amino acid residues are present between the leader and the MOMP, such amino acid residues form a fusion protein with the MOMP in the protein product. After expression of the nucleic acid molecule in the *E. coli* OM, the leader sequence is preferably cleaved from the MOMP protein or MOMP fusion protein, although in some cases, the leader sequence is not cleaved.

As noted above, the methods of the invention are useful for expression of MOMP fusion proteins in the OM of an *E. coli* host cell. To that end, in some embodiments the nucleic acid molecule, as described above, further comprises a sequence of nucleotides that encodes an additional polypeptide attached to the MOMP, wherein the polypeptide is selected from the group consisting of: a linker, an additional antigen, a polypeptide having adjuvant properties, a polypeptide for facilitating purification, a polypeptide for enhancing stability of the MOMP, a carrier protein, and a marker protein.

In embodiments of the invention directed to expression of MOMP fusion proteins in the OM of an *E. coli* cell, the additional polypeptide can be attached to the N-terminus of the MOMP or the C-terminus of the MOMP. In some embodiments of the invention, the additional polypeptide is attached to the C-terminus of the MOMP. In additional embodiments, the additional polypeptide is attached to the N-terminus of the MOMP. In preferred embodiments, the nucleic acid molecule comprises, from 5' to 3', a sequence of nucleotides that encodes a secretion leader for targeting the protein to the *E. coli* OM, a sequence of nucleotide that encodes *Chlamydia* MOMP, or a derivative thereof, and a sequence of nucleotides that encodes an additional polypeptide having the attributes described above. However, the invention also contemplates use of nucleic acid molecules that encode, from 5' to 3', a leader sequence, an additional polypeptide, and a MOMP or derivative thereof. One of skill in the art can readily determine whether a MOMP fusion protein made by the methods of the invention is expressed in the *E. coli* OM and whether the resulting fusion protein has the desired properties by using procedures known in the art of molecular and cell biology.

In embodiments of any of the methods of the invention described herein, the MOMP comprises, consists, or consists essentially of the *Chlamydia trachomatis* MOMP amino acid sequence set forth in SEQ ID NO:23 (serovar E), SEQ ID NO: 25 (serovar D), SEQ ID NO:26 (serovar G), SEQ ID NO:27 (serovar F), SEQ ID NO: 28 (serovar I), SEQ ID NO:29 (serovar J), or SEQ ID NO:30 (serovar H). In additional embodiments, the MOMP comprises, consists, or consists essentially of the *Chlamydia muridarium* MOMP amino acid sequence set forth in SEQ ID NO:31.

In additional embodiments of the invention, the methods comprise expression of *Chlamydia* MOMP derivatives in the *E. coli* OM. In some embodiments, such *Chlamydia* MOMP derivatives are derivatives of the sequences set forth in SEQ ID NO:23, SEQ ID NO:25, SEQ ID NO:26, SEQ ID NO:27, SEQ ID NO:28, SEQ ID NO:29, SEQ ID NO:30 or SEQ ID NO:31, wherein the derivative is at least 85%, at least 90%, at least 95%, at least 97%, or at least 99% identical to the reference sequence provided in SEQ ID NO:23, SEQ ID NO:25, SEQ ID NO:26, SEQ ID NO:27, SEQ ID NO:28, SEQ ID NO:29, SEQ ID NO:30 or SEQ ID NO:31.

In some embodiments, the MOMP derivative comprises amino acid residues that are deleted, inserted or substituted relative to the sequence of amino acids set forth in the MOMP sequences set forth in SEQ ID NO:23, SEQ ID NO:25, SEQ ID NO:26, SEQ ID NO:27, SEQ ID NO:28, SEQ ID NO:29, SEQ ID NO:30 or SEQ ID NO:31. In particular embodiments, the MOMP derivative comprises a number of amino acid substitutions, deletions or additions relative to the MOMP sequences disclosed herein, wherein the MOMP derivative comprises no more than 25 amino acid residues, no more than 20 amino acid residues, no more than 15 amino acid residues, no more than 12 amino acid residues, no more than 11 amino acid residues, no more than 10 amino acid residues, no more than 9 amino acid residues, no more than 8 amino acid residues, no more than 7 amino acid residues, no more than 6 amino acid residues, no more than 5 amino acid residues, no more than 4 amino acid residues, no more than 3 amino acid residues, no more than 2 amino acid residues, or 1 amino acid residue that is/are substituted, deleted or added relative to the MOMP sequences set forth in SEQ ID NO:23, SEQ ID NO:25, SEQ ID NO:26, SEQ ID NO:27, SEQ ID NO:28, SEQ ID NO:29, SEQ ID NO:30 or SEQ ID NO:31. In a particular embodiment, the *Chlamydia* MOMP derivative is a *Chlamydia trachomatis* (serovar D) derivative set forth in SEQ ID NO:24, which comprises a 2-amino acid substitution relative to SEQ ID NO:25, which was modified in order to increase Bam-site binding.

In embodiments of any of the methods of the invention, the leader sequence comprises the *Shigella flexneri* SopA sequence set forth in SEQ ID NO:8, the *Salmonella enterica* PgtE sequence set forth in SEQ ID NO:9, the *Yersinia pestis* Pla set forth in SEQ ID NO:10, the *E. coli* OmpP sequence set forth in SEQ ID NO:11, the *E. coli* OmpA sequence set forth in SEQ ID NO:12, or the pectate lysase B (PelB) sequence set forth in or SEQ ID NO:13 or derivative thereof. Thus, in embodiments of the invention, the leader sequence comprises a sequence of amino acids selected from the group consisting of: SEQ ID NO:8, SEQ ID NO:9, SEQ ID NO:10, SEQ ID NO:11, SEQ ID NO:12 and SEQ ID NO:13.

In alternative embodiments, the leader sequence comprises a sequence of amino acids that shares at least 90%, at least 95%, at least 97%, at least 98%, or at least 99% sequence identity with the amino acid sequence set forth in any of SEQ ID NO:8, SEQ ID NO:9, SEQ ID NO:10, SEQ ID NO:11, SEQ ID NO:12, or SEQ ID NO:13.

As stated above, the nucleic acid molecule used in the methods of the invention is operatively linked to a promoter. It is preferable that a low or moderate strength promoter is used in the methods of the invention. In some embodiments, the promoter is λPL or T7. It is also preferred that the expression vector is associated with a rate of transcription and/or translation that is constrainable to low or moderate. As used herein a constrainable to low or moderate transcription/translation rate can result from either elements in the vector itself or elements in the host cell. In some embodiments of the invention, the expression vector is pAVE029 or pACYDuet-1.

In any of the embodiments of any of the methods of the invention, the method may further comprise a step of inducing the transformed host cell with IPTG for from about 4 hours to about 6 hours. In additional embodiments, the step of inducing with IPTG is carried out for about 3.5 hours, about 4 hours, about 4.5 hours, about 5 hours, about 5.5 hours, about 6 hours or about 6.5 hours.

In some embodiments of the invention, the induction step described above is carried out at about 30° C.

In further embodiments, the cell density (OD590) is allowed to reach about 0.4 to about 0.8 before the induction step is carried out.

The invention also relates to a recombinant MOMP produced by any embodiment of any of the methods of the invention. The invention further relates to a recombinant MOMP derivative produced by the methods of the invention. In some embodiments, the MOMP derivative is a MOMP fusion protein or chimeric MOMP.

Pharmaceutical Compositions

The invention also relates to pharmaceutical compositions comprising a therapeutically or immunologically effective amount of a recombinant MOMP as described herein, formulated together with a pharmaceutically acceptable carrier or diluent.

To prepare pharmaceutical or sterile compositions of the invention, one or more recombinant *Chlamydia* MOMP is admixed with a pharmaceutically acceptable carrier or excipient. See, e.g., Remington's Pharmaceutical Sciences and U.S. Pharmacopeia: National Formulary, Mack Publishing Company, Easton, Pa. (1984). Pharmaceutically acceptable carriers include any and all solvents, dispersion media, isotonic and absorption delaying agents, and the like that are physiologically compatible, i.e. suitable for administration to humans. The carriers can be suitable for intravenous, intramuscular, subcutaneous, parenteral, rectal, spinal, or epidermal administration (e.g., by injection or infusion).

As used herein, the term "pharmaceutically acceptable carrier" refers to a substance, as described above, which is admixed with the recombinant MOMP (or derivative) of the invention that is suitable for administration to humans. In embodiments of the invention, the pharmaceutically acceptable carrier does not occur in nature in the same form, e.g. the substance is man-made, either because it does not exist in nature or the purity and/or sterility of the substance is not the same as the corresponding natural substance. For example, sterile water for injection, which is a sterile, bacteria-free, solute-free preparation of distilled water for injection, does not occur in nature in the same form and is considered a pharmaceutically acceptable carrier. In some embodiments, the pharmaceutical compositions of the invention comprise one or more recombinant MOMP or derivative thereof disclosed herein and sterile water for injection. In further embodiments, the pharmaceutically acceptable carrier may be another form of water that is appropriate for pharmaceutical or biological preparations and is not the same as water that occurs in nature, including purified water, water for injection, sterile purified water, and bacteriostatic water for injection.

In additional embodiments, the pharmaceutical compositions of the invention include a buffer as a pharmaceutically acceptable carrier. When a buffer is employed, the pH of the buffer is preferably in the range of about 5.5 to about 8.0. In additional embodiments, the pH is about 5.5 to about 7.5, about 5.5 to about 7.0, about 5.5 to about 6.5, about 6.0 to about 8.0, about 6.0 to about 7.5, about 6.0 to about 7.0, about 6.5 to about 7.0, about 6.0 to 6.5, about 6.0 to about 6.9, about 6.2 to about 6.75, or about 6.0 to about 6.75.

Pharmaceutical compositions typically should be sterile and stable under the conditions of manufacture and storage. Formulations of therapeutic and diagnostic agents may be prepared by mixing with acceptable carriers, excipients, or stabilizers in the form of, e.g., lyophilized powders, slurries, aqueous solutions, suspensions, microemulsions, dispersions, or liposomes, (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Sterile injectable solutions can be prepared by incorporating the active compound (i.e., one or more recombinant MOMP and optionally additional protein antigen) in the required therapeutically effective amount in an appropriate solvent with one or a combination of ingredients, as required, followed by filtered sterilization. Generally, dispersions are prepared by incorporating the active compound into a sterile vehicle that contains a basic dispersion medium and the required other ingredients. In the case of sterile powders for the preparation of sterile injectable solutions, the useful methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable pharmaceutical compositions can be brought about by including in the pharmaceutical composition an agent that delays absorption, for example, monostearate salts and gelatin. Additional agents, such as polysorbate 20 or polysorbate 80, may be added to enhance stability.

Toxicity and therapeutic efficacy of the pharmaceutical compositions of the invention, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, pharmaceutical compositions exhibiting high therapeutic indices are desirable. The data obtained from these cell culture assays and animal studies can be used in formulating a range of dosage for use in human. The dosage in such pharmaceutical compositions lies preferably within a range of circulating concentrations that include the $ED_{50}$ with little or no toxicity. The dosage may vary within this range depending upon the dosage form employed and the route of administration.

In some embodiments of the invention, the pharmaceutical compositions of any embodiment herein can further comprise one or more additional rMOMP antigens produced by the methods of the invention, or derivative thereof, and/or one or more additional non-MOMP *Chlamydia* antigens. In specific embodiments, the pharmaceutical composition comprises, in addition to a pharmaceutically acceptable carrier, at least one recombinant MOMP comprising a sequence of amino acids as set forth in SEQ ID NO:23, SEQ ID NO:24, SEQ ID NO:25, SEQ ID NO:26, SEQ ID NO:27, SEQ ID NO:28, SEQ ID NO:29, or SEQ ID NO:30, or derivative thereof, wherein the rMOMP is produced by the methods of the invention. In additional embodiments, the pharmaceutical composition comprises two rMOMP of the invention, or derivatives thereof. In additional embodiments, the pharmaceutical composition comprises three, four, five, six, seven, eight, or more rMOMP of the invention, or derivatives thereof. The pharmaceutical compositions of the invention can comprise more than one rMOMP as set forth herein, more than one rMOMP derivative, or a combination of one or more rMOMP of the invention and one or more rMOMP derivative of the invention. In additional embodiments, the pharmaceutical composition comprises at least one rMOMP produced by the methods herein, or derivative thereof, and at least one additional *Chlamydia* antigen that is not a MOMP or derivative.

In further embodiments of this aspect of the invention, the pharmaceutical compositions comprise one or more recombinant MOMP or derivative thereof produced by the methods disclosed herein, a pharmaceutically acceptable carrier, and an adjuvant. The inclusion of adjuvants may augment the immune response elicited by administration of the vaccine antigens (e.g. rMOMP or rMOMP derivative and optionally additional *Chlamydia* antigens) to a patient, in order to induce long lasting protective immunity. In addition to increasing the immune response, adjuvants may be used to decrease the amount of antigen necessary to provoke the desired immune response or decrease the number of injections needed in a clinical regimen to induce a durable immune response and to provide protection from disease and/or induce regression of disease caused by *Chlamydia* infection.

Adjuvants that may be used in conjunction with the pharmaceutical compositions of the invention, include, but are not limited to, montanide, adjuvants containing CpG oligonucleotides, or other molecules acting on toll-like receptors such as TLR4 and TLR9 (for reviews, see, Daubenberger, C. A., *Curr. Opin. Mol. Ther.* 9(1):45-52 (2007); Duthie et al., *Immunological Reviews* 239(1): 178-196 (2011); Hedayat et al., *Medicinal Research Reviews* 32(2): 294-325 (2012)), including lipopolysaccharide, monophosphoryl lipid A, and aminoalkyl glucosaminide 4-phosphates. Additional adjuvants useful in the pharmaceutical compositions of the invention include immunostimulatory oligonucleotides (IMO's; see, e.g. U.S. Pat. Nos. 7,713,535 and 7,470,674, such as IMO-2055, as disclosed in the Examples herein); T-helper epitopes, lipid-A and derivatives or variants thereof, liposomes, calcium phosphate, cytokines, (e.g. granulocyte macrophage-colony stimulating factor (GM-CSF) IL-2, IFN-α, Flt-3L), CD40, CD28, CD70, IL-12, heat-shock protein (HSP) 90, CD134 (OX40), CD137, CoVaccine HT, non-ionic block copolymers, incomplete Freund's adjuvant, chemokines, cholera toxin; *E. coli* heat-labile enterotoxin; pertussis toxin; muramyl dipeptide, muramyl peptide analogues, MF59, SAF, immunostimulatory complexes, biodegradable microspheres, polyphosphazene; and polynucleotides.

Additional adjuvants for use with the pharmaceutical compositions described herein are adjuvants containing saponins (e.g. QS21), either alone or combined with cholesterol and phospholipid in the characteristic form of an ISCOM ("immune stimulating complex," for review, see Barr and Mitchell, *Immunology and Cell Biology* 74: 8-25 (1996); and Skene and Sutton, *Methods* 40: 53-59 (2006)). Such adjuvants are referred to herein as "saponin-based adjuvants". In specific embodiments of the pharmaceutical compositions and methods provided herein, the recombinant MOMP antigens are combined with an ISCOM-type adjuvant or "ISCOM", which is an ISCOM matrix particle adjuvant, such as ISCOMATRIX™, which is manufactured without antigen (ISCOM™ and ISCOMATRIX™ are the registered trademarks of CSL Limited, Parkville, Australia).

Additionally, aluminum-based compounds, such as aluminum hydroxide ($Al(OH)_3$), aluminum hydroxyphosphate ($AlPO_4$), amorphous aluminum hydroxyphosphate sulfate (AAHS) or so-called "alum" ($KAl(SO_4).12H_2O$) (see Klein et al., Analysis of aluminum hydroxyphosphate vaccine adjuvants by Al MAS NMR., *J. Pharm. Sci.* 89(3): 311-21 (2000)), may be combined with the pharmaceutical compositions provided herein.

In some embodiments described herein, the adjuvant is an aluminum salt adjuvant. In alternative embodiments, the adjuvant is a saponin-based adjuvant or a toll-like receptor agonist adjuvant. In exemplary embodiments of the invention provided herein, the aluminum adjuvant is aluminum hydroxyphosphate or AAHS, alternatively referred to as "MAA". In alternative embodiments, the adjuvant is aluminum hydroxide. In further embodiments, the adjuvant is aluminum phosphate.

Adjuvants may be combined to provoke the desired immune response. For example, the pharmaceutical compositions of the invention may comprise at least one rMOMP produced by the methods described herein, a pharmaceutically acceptable carrier and a combination of two or more adjuvants. In some embodiments of the invention, the pharmaceutical compositions comprise an aluminum salt adjuvant and a second adjuvant. In other embodiments, the compositions comprise an aluminum salt adjuvant and a second adjuvant selected from a saponin adjuvant and a toll-like receptor agonist.

Methods of Use

Embodiments of the invention also include one or more of the recombinant MOMP, or derivative thereof, or pharmaceutical compositions comprising said recombinant MOMP or derivative, or a vaccine comprising said recombinant MOMP or pharmaceutical compositions (i) for use in, (ii) for use as a medicament or composition for, or (iii) for use in the preparation of a medicament for: (a) therapy (e.g., of the human body); (b) medicine; (c) inhibition of *Chlamydia* replication; (d) treatment or prophylaxis of infection by *Chlamydia*; (e) prevention of recurrence of *Chlamydia* infection; (f) reduction of the progression, onset or severity of pathological symptoms associated with *Chlamydia* infection and/or reduction of the likelihood of a *Chlamydia* infection or, (g) treatment, prophylaxis of, or delay in the onset, severity, or progression of *Chlamydia*-associated disease(s), including, but not limited to: oculogenital disease, cervicitis, urethritis, endometritis, pelvic inflammatory disease, tubal infertility, ectopic pregnancy, neonatal conjunctivitis, and infant pneumonia. In the uses set forth herein, the recombinant MOMP or derivatives thereof, pharmaceutical compositions and/or vaccines comprising or consisting of said recombinant MOMP can optionally be employed in combination with one or more additional therapeutic agents, for example, a second vaccine for a different pathogen.

Thus, the invention relates to a method as set forth above, which method comprises administration of an immunologically or therapeutically effective amount of any rMOMP or rMOMP derivative produced by the methods of the invention, or pharmaceutical composition or vaccine thereof, to a patient in need thereof, whereby administration to the patient results in any of (c) through (g) above.

The mode of administration to the patient can vary and may include oral, rectal, transmucosal, intestinal, parenteral; intramuscular, subcutaneous, intradermal, intrathecal, direct intraventricular, intravenous, intraperitoneal, intranasal, intraocular, inhalation, insufflation, topical, cutaneous, transdermal, or intra-arterial. In embodiments of the invention, the route of administration is parenteral. In specific embodiments of the invention, the mode of administration is subcutaneous or intraperitoneal. In additional embodiments of the invention, the route of administration is intramuscular, intradermal, or subcutaneous.

The rMOMP, derivatives, or pharmaceutical compositions of the invention can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

Codon-Harmonized MOMP Nucleotide Sequences

One aspect of the invention relates to codon harmonized nucleic acid molecules encoding *Chlamydia* MOMP or a derivative thereof, or encoding *Chlamydia* MOMP plus a leader sequence for targeting the MOMP to the outer membrane of the cell. In particular embodiments, the invention provides a nucleic acid molecule that encodes the *Chlamydia trachomatis* MOMP set forth in SEQ ID NO:23, SEQ ID NO: 25, SEQ ID NO:26, SEQ ID NO:27, SEQ ID NO: 28, SEQ ID NO:29, SEQ ID NO:30, wherein the nucleic acid molecule is codon-harmonized. The invention also provides a codon-harmonized nucleic acid molecule that encodes the *Chlamydia muridarium* MOMP set forth in SEQ ID NO:31.

In additional embodiments, the invention provides codon-harmonized nucleic acid molecules that encode variants or derivatives of the *Chlamydia* MOMP amino acid sequences described herein. Thus, the invention relates to codon-harmonized nucleic acid molecules encoding derivatives of the *Chlamydia* MOMP sequences set forth in SEQ ID NO:23, SEQ ID NO:25, SEQ ID NO:26, SEQ ID NO:27, SEQ ID NO:28, SEQ ID NO:29, SEQ ID NO:30 or SEQ ID NO:31, wherein the derivative is at least 85%, at least 90%, at least 95%, at least 97%, or at least 99% identical to the reference sequence provided in SEQ ID NO:23, SEQ ID NO:25, SEQ ID NO:26, SEQ ID NO:27, SEQ ID NO:28, SEQ ID NO:29, SEQ ID NO:30 or SEQ ID NO:31.

In some embodiments, the codon-harmonized nucleic acid molecule encodes a MOMP derivative that comprises amino acid residues that are deleted, inserted or substituted relative to the sequence of amino acids set forth in the MOMP sequences set forth in SEQ ID NO:23, SEQ ID NO:25, SEQ ID NO:26, SEQ ID NO:27, SEQ ID NO:28, SEQ ID NO:29, SEQ ID NO:30 or SEQ ID NO:31. In particular embodiments, the MOMP derivative comprises a number of amino acid substitutions, deletions or additions relative to the MOMP sequences disclosed herein, wherein the MOMP derivative comprises no more than 25 amino acid residues, no more than 20 amino acid residues, no more than 15 amino acid residues, no more than 12 amino acid residues, no more than 11 amino acid residues, no more than 10 amino acid residues, no more than 9 amino acid residues, no more than 8 amino acid residues, no more than 7 amino acid residues, no more than 6 amino acid residues, no more than 5 amino acid residues, no more than 4 amino acid residues, no more than 3 amino acid residues, no more than 2 amino acid residues, or 1 amino acid residue that is/are substituted, deleted or added relative to the MOMP sequences set forth in SEQ ID NO:23, SEQ ID NO:25, SEQ ID NO:26, SEQ ID NO:27, SEQ ID NO:28, SEQ ID NO:29, SEQ ID NO:30 or SEQ ID NO:31. In a particular embodiment, the codon-harmonized nucleic acid molecule encodes the *Chlamydia trachomatis* (serovar D) derivative set forth in SEQ ID NO:24, which comprises a 2-amino acid substitution relative to SEQ ID NO:25, which was modified in order to increase Bam-site binding.

The invention further relates to nucleic acid molecules that encode a *Chlamydia* MOMP polypeptide and a leader sequence for targeting the MOMP to the OM of the cell, wherein the nucleic acid molecules are codon-harmonized.

In some embodiments, the *Chlamydia* MOMP is any MOMP polypeptide sequence or MOMP derivative polypeptide sequence disclosed herein, and the leader sequence comprises the *Shigella flexneri* SopA sequence set forth in SEQ ID NO:8, the *Salmonella enterica* PgtE sequence set forth in SEQ ID NO:9, the *Yersinia pestis* Pla set forth in SEQ ID NO:10, the *E. coli* OmpP sequence set forth in SEQ ID NO:11, the *E. coli* OmpA sequence set forth in SEQ ID NO:12, or the pectate lysase B (PelB) sequence set forth in or SEQ ID NO:13. In particular embodiments, the codon-harmonized nucleic acid molecule encodes a *Chlamydia* MOMP+leader sequence set forth in SEQ ID NO:16, SEQ ID NO:19, or SEQ ID NO:22. In additional particular embodiments, the nucleic acid molecule that encodes the *Chlamydia* MOMP+leader sequence comprises a sequence of nucleic acids as set forth in SEQ ID NO:15, SEQ ID NO:18, or SEQ ID NO:21, or a nucleic acid derivative thereof.

All publications mentioned herein are incorporated by reference for the purpose of describing and disclosing methodologies and materials that might be used in connection with the present invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

Expression of Recombinant *Chlamydia* MOMP.

A. Codon Harmonization.

β-barrel membrane protein expression directed to the *E. coli* outer membrane (OM expression) is typically challenging. We evaluated the effect of codon selection on the surface expression of full length recombinant *Chlamydia* MOMP (rMOMP). We performed codon harmonization and standard codon optimization on the recombinant MOMP gene and evaluated outer membrane expression with a whole cell flow cytometry binding assay using anti-Chlamydial EB mouse sera. Both genes were expressed in a pET vector expression system and with a native *Chlamydia muridarium* (Cm) MOMP leader sequence (Tables 2 and 3). We observed that codon harmonization resulted in ~2 fold increase in outer membrane expression of recombinant *Chlamydia muridarium* MOMP, compared to the standard host codon optimized gene (FIG. 1), suggesting that better protein folding and OM expression were achieved with the codon harmonized gene regulating the rate of translation. Upon this finding, codon harmonized rMOMP genes have been used in subsequent expression evaluations (such as optimal expression vectors and leader sequences) to further improve rMOMP OM expression.

B. Expression Vector Optimization.

A panel of *E. coli* expression vectors were evaluated to further increase the surface expression level of rMOMP (Table 2). The key elements that could affect the OM expression include promoter strength and vector copy number. We compared vectors with high, medium or low copy numbers, with promoters of high, moderate or titratable strength. We found that either a strong promoter or a high vector copy number limited the surface expression of rMOMP (Table 2). Higher rMOMP surface expression was achieved with a combination of moderate promoter and a low vector copy number (such as pAVE029), suggesting that lower transcription level is preferred. Consistently, reasonable rMOMP OM expression level can be obtained with a pACYDuet vector when we used a host strain with a controllable RNA polymerase level to reduce the rMOMP mRNA transcription rate. We hypothesized that slower transcription and therefore slower translation is optimal for rMOMP OM expression as it provides ample time to allow the newly synthesized protein to properly fold and translocate onto the outer membrane, resulting in an increased level of surface expression. This result is also consistent with our observations on the effect of gene codon usage harmonization described above.

TABLE 2

Evaluation of *E. coli* expression vectors

| Vector | Promoter/ Strength | Inducer | Origin of Replication | Copy Number | rMOMP Surface Expression (GFI*) |
|---|---|---|---|---|---|
| **pAVE029 | λPL/ Moderate | IPTG | pAT153(colE1) | Low | Good (~300) |
| pACYDuet-1 | T7/ Titratable | Arabinose + IPTG | p15A | Low | Intermediate (~120) |
| pET (pETBlue-1 and pET22b) | T7/Strong | IPTG | pUC | High | Low(~30 or lower) |
| pWSK29 | T7/T3/ Strong | IPTG | pSC101 | Low | None (intracellular) |
| pJ831(pUC) | T7/ Titratable | Rhamnose | pMB1 | High | None (intracellular) |
| pJ841(pBR) | T7/ Titratable | Rhamnose | pMB1 | Medium | None (intracellular) |
| pJ851(pACYC) | T7/ Titratable | Rhamnose | p15A | Low | None (intracellular) |

*GFI: geomean fluorescence intensity from whole cell flow cytometry binding assay

**pAVE029 is an *E. coli* RNA polymerase dependent expression vector. Others listed are bacteriophage T7 RNA polymerase dependent expression vectors.

C. Secretion Leader Sequence Optimization.

In order to better direct the OM localization of rMOMP, we evaluated different secretion leader sequences which might help the OM localization of the target protein (Table 3). Among tested leader sequences, *E. coli* OmpA leader and OmpP leader resulted in the highest rMOMP OM expression. However, incomplete cleavage of the OmpP leader was observed and heterologous forms of rMOMP were generated (data not shown). Omptins leader family and PelB leader resulted in similar levels of moderate surface expression of rMOMP. Native Cm MOMP leader is able to direct the OM expression for CmMOMP, but not for CtD or CtE MOMP. Neither native CtD or CtE MOMP leaders result in the surface expression of rMOMP.

TABLE 3

| Secretion Leader | | rMOMP Surface Expression | | |
|---|---|---|---|---|
| Sequences Evaluated | Secretion Leader Sequences | Cm_MOMP | CtD_CT_MOMP | CtE_MOMP |
| Native Cm MOMP | MKKLLKSVLAFAVLGSASSLHA (SEQ ID NO: 6) | + | - | - |
| Native CtD/CtE MOMP | MKKLLKSVLVFAALGSASSLQA (SEQ ID NO: 7) | ND | - | - |
| **Shigella flexneri* (SopA) | MKSKFLVLALCVPAIFTTHA (SEQ ID NO: 8) | ND | ND | + |

TABLE 3-continued

| Secretion Leader Sequences Evaluated | Secretion Leader Sequences | rMOMP Surface Expression Cm_MOMP | CtD_CT_MOMP | CtE_MOMP |
|---|---|---|---|---|
| **salmonella enterica* (PgtE) | MKTHVIAVMIIAVFSESVYA (SEQ ID NO: 9) | ND | ND | + |
| **Yersinia pestis* (Pla) | MKKSSIVATIITILSGSANA (SEQ ID NO: 10) | ND | ND | + |
| *E.coli*. OmpP | MQTKLLAIMLAAPVVFSSQEASA (SEQ ID NO: 11) | ND | ND | ++ |
| *E*.coli. OmpA | MKKTAIAIAVALAGFATVAQA (SEQ ID NO: 12) | + | ND | ++ |
| pectate lyase B of *Erwinia carotovora* CE (PelB) | MKYLLPTAAAGLLLLAAQPAMA (SEQ ID NO: 13) | + | + | + |

*Belongs to omptins leader sequence family (trans membrane aspartic proteases)
ND: Not Determined
Cm: *C. muridarium*
CtD_CT: *C. trachomatis* Serovar D (C terminal AA sequence modified)
CtE: *C. trachomatis* SerovarE D. Optimization of Expression Conditions.

We evaluated many expression conditions with the pAVE029 expression system that could impact rMOMP OM expression, including cell culture medium, cell density at induction, induction time and temperature (FIG. 2). rCtE MOMP with a PelB leader sequence was used in this evaluation. We performed induction for 4 hrs, 6 hrs and 16 hrs under four different temperatures: 16° C., 25° C., 30° C. and 37° C. We found that 4 hrs and 6 hrs of IPTG induction resulted in comparable rMOMP OM expression levels while no expression was observed for 16 hrs induction at any of the temperatures tested (FIG. 2A). Induction at 37° C. or 30° C. resulted in high surface expression of rMOMP (FIG. 2A). However, we observed cell fragility at 37° C., indicated by the decreased OD590 after induction (FIG. 2B). We also performed induction at different cell densities and found that it dramatically impacts the rMOMP surface expression. We obtained the highest rMOMP expression with an induction OD590 of ~0.5, while expression dropped with an induction OD590 of ~0.8, and little or no expression with an induction OD590 of 1.2 or higher (FIG. 2C).

Seven different cell culture media were evaluated for their effect on expression level: 1-LB (Luria broth), 2-2YT (2× yeast extract and tryptone)+1% Glu, 3-Mg, 4-ProGro™ (Expression Technologies, Inc., San Diego, Calif.), 5-Azura, 6-Cinnabar, and 7-Auto induction medium). Interestingly, we observed very different rMOMP OM expression (FIG. 2D). We obtained very high level of periplasmic rMOMP expression (data not shown) with Progro medium, however, no surface expression was observed. Low levels of rMOMP OM expression were observed with LB medium, 0.2% lactose auto induction medium, 2YT medium with 1% glucose, and the chemically defined Azura medium. The highest rMOMP OM expression (GFI ~300 to 400 in the whole cell flow cytometry binding assay) was obtained with growth in Cinnabar medium, resulting in a visible rMOMP band on a SDS-PAGE gel. IPTG concentration for induction was also evaluated and comparable rMOMP OM expression was observed with 0.1 mM to 1 mM IPTG (data not shown). Therefore, expression studies described herein were induced by addition of 0.4 mM IPTG.

In summary, the most optimized conditions we have obtained for rMOMP OM expression is to perform induction for 4 hrs at 30° C. when cell density (OD590) reaches ~0.5 (FIG. 3). The optimal expression level is increased ~10 fold compared to the original expression conditions. Three different rMOMP proteins (Cm, CtD and CtE) have been successfully expressed on *E. coli* outer membrane under these conditions.

Example 2

Purification of Recombinant *Chlamydia* MOMP.

Harvested *E. coli* cells expressing recombinant MOMP were disrupted by microfluidization and membrane fraction containing rMOMP was pelleted by ultracentrifugation, while soluble cellular proteins were largely separated. Washing the membrane fraction with high salt buffer further removed residual soluble cellular proteins. Subsequent wash with a buffer containing 1% triton X-100 detergent removed the bacterial inner membrane and wash with a buffer containing 3% beta-octyl-glucoside detergent removed certain bacterial outer membrane proteins other than recombinant MOMP. After these steps, rMOMP became the most abundant protein in the membrane fraction. A variety of detergents were evaluated for extraction of rMOMP from the outer membrane. We found that sarkosyl (an anionic detergent) was the most efficient, followed by foscholine-14 (a lipid like zwitterionic detergent) and zwittergent 3-12. DTT was required for extraction of rMOMP. The extraction contained ~60% rMOMP. Extracted rMOMP was further purified by size exclusion and ion exchange chromatography. The purified rMOMP migrates very similarly to the native MOMP (nMOMP) protein that was purified from *Chlamydia* elementary body (EB) on a SDS-PAGE gel, with slightly higher amounts of dimeric and oligomeric forms (FIGS. 4A and 4B). In-solution mass spectrometry suggested that final purified rCtE-MOMP is about 70% pure with a few co-purified *E. coli* proteins (FIG. 4C). The endotoxin level in the final purified protein sample is undetectable with an anti-*E. coli* LPS mAb on western blot (FIG. 4D) or in the LAL assay (data not shown).

Example 3

Mouse Immunogenicity and Challenge Study

Female C57BL/6 mice (32 per group) were immunized by subcutaneous (s.c.) routes with purified nMOMP or rMOMP (10 µg/mouse/immunization) in combination with an adjuvant containing IMO-2055 and Montanide ISA 720 VG. Two preparations of rCtE-MOMP were evaluated: one with a PelB leader sequence and the other one with an OmpA leader sequence. A positive control group was immunized with $1 \times 10^6$ live EB in SPG per mouse by intraperitoneal (i.p.) route. A negative control group (adjuvant control) was administered with a combination of IMO-2055 and Montanide ISA 720 VG only.

Post-immunization mouse serum was analyzed by ELISA with CtD EBs as the coating antigen (FIG. 5). In general, the rMOMP immunized mice groups tended to have more variability in titers, compared to nMOMP immunized mice group. The PelB-leader-rMOMP immunized mice have comparable (no statistical different) IgGFcγ titers and slightly lower IgG1 and IgG2c titers compared to the nMOMP immunized group. The OmpA-leader-rMOMP immunized mice have lower IgGFcγ, IgG1 and IgG2c titers than the nMOMP immunized group. Two weeks following the last immunization, mice were challenged intravaginally with CtD EBs. The vaginal vault and ectocervix were swabbed on multiple time points following challenge and *Chlamydia* copy numbers were evaluated by real-time PCR. For each animal, qPCR values were log transformed at each time point and AUC (area under curve) value was calculated for the time period (FIG. 6). Both preparations of the rCtE-MOMP (with a PelB leader or with an OmpA leader) elicited statistical significant protective responses ($p<0.01$) in immunized mice, compared to the group that received the adjuvant only (FIG. 6). Moreover, the level of protection from bacterial challenge in mice immunized with the PelB-leader-rMOMP was comparable (similar bacterial load post challenge) to the level in nMOMP immunized group. The level of protection from bacterial challenge in the OmpA-leader-rMOMP immunized mice was slightly lower (higher bacterial load post challenge) than the level in nMOMP immunized group, consistent with the lower overall IgG antibody titers induced in this group.

Our data suggested that the recombinant MOMP expressed on and purified from the outer membrane of *E. coli* elicits protective serum antibody responses in a mouse challenge model, therefore, can be evaluated as a potential candidate for a vaccine against *Chlamydia.*

Materials and Methods:

Example 4

Codon Harmonization of the *Chlamydia* MOMP Gene for Recombinant Expression

Nucleotide sequences of the gene encoding the Major Outer Membrane Protein (MOMP) were retrieved from Merck internal website CMR (Comprehensive Microbial Resources) for the following strains: *C. muridarum* Nigg (strain MoPn) ORF TC0052 (GenBank Gene ID: 1245581; Protein Accession No. P75024.1); *C. trachomatis* strain D/UW-3/CX CT ORF TC 681 Serovar D (GenBank Gene ID: 884473; Protein Accession No. NP 220200.1); and *C. trachomatis* strain E/12-94 ORF 0175_03780 Serovar E (GenBank Gene ID: 16635280; Protein Accession No. P17451). Amino acid sequences consisting of a secretion leader and the mature MOMP protein (Table 3) were codon harmonized (Angov et al., *Plos One* 3(5):1-10 (2008)). In brief, the codon usage data for *Chlamydia* (native host) and *E. coli* (expression host) was obtained from the Codon Usage Database (tabulated from NCBI-Genbank, Kazusa DNA Res. Inst., Kisarazu, Japan). For each species, the strain with the most codon usage data available was selected as a representative. The codon usage frequency for both native and expression hosts was then calculated and a reference database was generated. We first identified the amino acid residues for which the rare codons were used in the native host, and the corresponding rare codon in the expression host was selected for those residues. For the remaining residues, the codon in the expression host that has the closest frequency (less than 15% difference) to the corresponding codon in the native host was selected. If a codon in *E. coli* could not be identified that had less than 15% difference relative to the frequency of the native codon, a codon with 15% or more lower frequency was chosen if the residue was in a "linker/hinge" region in order to slow down the translation speed and a codon with 15% or more higher frequency was selected if the residue was outside the linker region to achieve higher expression. Once the harmonized gene sequence for *Chlamydia* MOMP was generated, NdeI and XhoI restriction enzyme sites were mutated for subsequent cloning.

Example 5

Cloning and Expression of Recombinant *Chlamydia* MOMP

The harmonized gene sequences with flanking NdeI and XhoI restriction enzyme sites were synthesized and cloned into the PUC57 cloning vector. The synthesized genes were excised from PUC57 vector through NdeI and XhoI restriction sites. The excised DNA fragments were ligated into the pAVE029 expression vector (MSD Biologics UK) using T4 DNA ligase (Promega Corp., Madison, Wis.) for 4 hours at 16° C. Ligated plasmids were transformed into competent cells DH5a (Invitrogen, Carlsbad, Calif.) and grown in LB agar plates with 10 μg/mL tetracycline. Colonies harboring the recombinant plasmid were identified by PCR and confirmed by sequencing using pAVE029 vector specific primers for 5' end of the gene (ppop40 primer ATT CTG CAT TCA CTG GCC GAG G (SEQ ID NO:1)) and 3' end of the gene (T7 Term standard sequencing primer GCT AGT TAT TGC TCA GCG G (SEQ ID NO:2)). The sequence-confirmed positive colonies were propagated in LB medium with 10 μg/mL of tetracycline and plasmid DNA was isolated from the cell cultures with a HiSpeed Maxi Kit (QIAGEN, Venlo, Netherlands).

The recombinant plasmid DNA was transformed by electroporation into an expression host strain *E. coli* K12 W25113 using a Bio-Rad GenePulser (Bio-Rad Laboratories, Inc., Hercules, Calif. Transformed cells were plated on LB Agar plates with 10 μg/mL tetracycline and grown overnight at 37° C. Single colonies were picked and inoculated into Cinnabar media (Teknova, Hollister, Calif.) with 10 μg/mL of tetracycline and grown at 37° C. with shaking at 250 RPM until OD600 reaches to mid log phase (~0.5). 0.4 mM IPTG was added into the cell culture for induction and the cell culture was incubated for 4 hours at 30° C. with shaking. The cell cultures were then characterized by whole cell flow cytometry binding assay, SDS-PAGE, and Western Blot analysis.

Example 6

Whole Cell Flow Cytometry Binding

50 μL of *E. coli* cell culture (at 1×10$^9$ cells/mL) that recombinantly expressed *Chlamydia* MOMP was incubated with 50 μL of mouse sera against *Chlamydia* elementary body (EB) at a dilution of 1:250 for 1 hour at room temperature in a 96 well plate. After incubation, the cells were washed with 1 mL phosphate buffered saline (PBS) and stained with 100 μL of a fluorescence labeled secondary antibody (Alexa Fluo-488 F(ab)'2 fragment of goat anti-mouse IgG (H+L), Life Technologies, Carlsbad, Calif.) at a dilution of 1:100. The stained cells were washed twice and re-suspended in PBS for flow cytometric analysis (Guava Technologies, EMD Millipore, Billerica, Mass.). Data analyses were performed with CytoSoft 5.3 software (Guava Technologies).

Example 7

SDS-PAGE and Western Blot

*E. coli* cell culture (~$1\times10^9$ cells) that recombinantly expresses *Chlamydia* MOMP was treated with SDS loading buffer with reducing agent (Invitrogen, Carlsbad, Calif.). Samples were applied to NuPAGE (Invitrogen) gel electrophoresis. NuPAGE gel was stained with Gel code blue staining solution (Pierce Biotechnology, Rockford, Ill.). For Western Blot, samples were applied to gel electrophoresis and then electro-transferred onto nitrocellulose membranes (Life Technologies, Carlsbad, Calif.). The membranes were incubated with mouse sera against *Chlamydia* EB (or other specific primary antibodies) followed by a fluorescence conjugated goat anti-mouse secondary antibody (IRDye 680LT, Licor). Image was acquired and analyzed by LICOR ODYSSEY® (Li-Cor Biosciences, Lincoln Nebr.).

Example 8

Purification of Recombinant *Chlamydia* MOMP

*E. coli* cell culture was grown in Cinnabar media (Teknova, Hollister, Calif.) and induced by IPTG as described above. Cell culture was harvested by centrifugation at 12,000 g for 15 min. Cell pellets were weighed and resuspended in 9 volumes (v/w) of 50 mM Tris-Cl pH 8.0 buffer with EDTA free protease inhibitor (Roche, Basel, Switzerland, 1 tab per 100 mL buffer). Cells were disrupted by microfluidization and undisrupted cells were pelleted and removed by centrifugation at 9700 g for 15 min. Membrane fraction was pelleted by centrifugation of the cleared disrupted cells at 23800 g for 90 min and washed with high salt buffer (1M NaCl, 0.05% tween20) followed by another centrifugation at 23800 g for 90 min. To remove the bacterial inner membrane, washed membrane fraction was resuspended in buffer A (20 mM Tris-Cl pH 8.0, 1 mM EDTA) with 1% triton X-100, incubated at room temperature for 15 min followed by ultracentrifugation at 120,000 g for 40 min. To remove bacterial outer membrane proteins other than recombinant MOMP (rMOMP), pellets were resuspended by buffer A (20 mM Tris-Cl pH 8.0, 1 mM EDTA) with 3% beta-octyl-glucoside, incubated at room temperature for 1 hour followed by ultracentrifugation at 120,000 g for 40 min. rMOMP was extracted by resuspending the pellets in buffer A (20 mM Tris-Cl pH 8.0, 1 mM EDTA) with 1% sarkosyl, incubated at room temperature for 2 hour followed by ultracentrifugation at 120,000 g for 40 min. Extracted rMOMP was subjected to size exclusion chromatography (Sephacryl S300, GE healthcare) in a buffer containing 10 mM Hepes pH 7.3, 150 mM NaCl, 0.1% zwittergent 3-14. Eluted rMOMP was further purified with ion exchange chromatography (Hitrap Q FF, GE healthcare). Purified rMOMP fractions were pooled and stored at 4° C.

Example 9

Cell Culture and Propagation of Chlamydiae

All cell lines and *Chlamydia* strains were obtained from ATCC (Manassas, Va.). HeLa 229 cells were used for propagation all strains. HeLa 229 cells were grown in Eagle's Minimal Essential Medium (ATCC) supplemented with 10% heat-inactivated fetal bovine serum (FBS, Hyclone), 50 μg/mL vancomycin (Sigma-Aldrich, St. Louis, Mo.), and 10 μg/mL gentamicin (Gibco). Host cells were seeded into tissue culture flasks at a cell density of $5\times10^5$ cells/mL and incubated overnight at 37° C. in 5% $CO_2$ to achieve a confluent monolayer. Cell monolayers were infected with *C. trachomatis* (Ct) strain D/UW-2/Cx stock diluted in sucrose-phosphate-glutamate (SPG) buffer and cultured for 72 hours. The Chlamydiae were harvested from the infected cells and purified by centrifugation through 30% Renograffin (Bracco Diagnostics, Milan Italy) and stored frozen at −80° C.

Example 10

Mouse Immunization

Female C57BL/6 mice (Taconic Farms) were used at 6 to 8 weeks of age, and food and water were provided ad libitum. All animal procedures were in accordance with government and institutional guidelines for animal health and well-being, and were approved by the Merck Institutional Animal Care and Use Committee.

Animals were immunized by subcutaneous (s.c.) routes with rMOMP (1 to 10 μg/mouse/immunization) in combination with an adjuvant containing IMO-2055 and Montanide ISA 720 VG (SEPPIC Inc., Coley Pharmaceutical Group Inc., Wellesley, Mass.) at a ratio of 70:30 (v/v). Live EB groups were immunized with $1\times10^6$ EB in SPG per mouse by intraperitoneal (i.p.) route. Adjuvant control groups were administered with a combination of IMO-2055 and Montanide ISA 720 VG only. Immunizations were administered on days 0, 20 and 30.

Prior to the first immunization and two weeks following the final immunization, tail bleeds were performed with blood collected in BD Microtainer® Serum Separator Tubes (Becton, Dickinson and Company, Franklin Lakes, N.J.). Blood samples were centrifuged at 6,000 rpm for 5 min and serum was transferred to a microcentrifuge tube.

Example 11

Murine Challenge Study

At approximately 2 weeks following the last immunization, progesterone (medroxyprogesterone acetate, Depo-Provera; Pfizer, New York, N.Y.) was administered subcutaneously (2.5 mg/dose) at 10 and 3 days before challenge. Mice were challenged intravaginally (approximately 1 month following the last immunization) by direct instillation of 10 μL of SPG containing $1\times10^5$ Ct serovar D EBs. The vaginal vault and ectocervix were swabbed using a microfiber swab (Fisher, Hampton, N.H.) on days 7, 11, 14, 18, and 21 (or a combination of these time points) following challenge.

Swabs were placed into a 1.5-mL tube containing 2 sterile glass beads (5 mm diameter) and 300 μL of *Chlamydia* isolation medium (Trinity Biotech, Bray, Ireland) on ice. Bacteria were eluted from the swabs and separated from cells by vortexing for 60 seconds. 100 µL of eluted cells/bacteria were plated onto a processing cartridge containing 100 µL of PBS and stored at −70° C. until DNA extraction.

Example 12

Primer, Probe and Real-Time PCR

DNA from genital swab samples was extracted using the MagNA Pure 96 DNA and Viral NA small volume kit (Roche, Basel, Switzerland) on the MagNA pure machine (Roche) according to the manufacturer's instructions.

The oligonucleotide primer set was designed for detection of all species of Chlamydiae. The sense primer, 16S DIR 5'-CGC CTG AGG AGT ACA CTC GC-3' (SEQ ID NO:3), and anti-sense primer, 16S Rev 5'-CCA ACA CCT CAC GGC ACG AG-3' (SEQ ID NO:4), were designed to amplify a 208-bp fragment of the chlamydial 16S ribosomal subunit gene, conserved across Chlamydia strains and serovars. Primers were obtained from Sigma Genosys (The Woodlands, Tex.), and the probe, 16S Fam-5'-CAC AAG CAG TGG AGC ATG TGG TTT AA-3' Tamra (SEQ ID NO:5), was synthesized by Applied Biosystems, (Foster City, Calif.).

The 50-µL reaction mixtures consisted of 1× QuantiTect Multiplex PCR master mix without ROX (Qiagen, venlo, netherlands), 100 nmol/L 16S probe, 200 nmol/L primer 16S DIR, 400 nmol/L primer 16S Rev, 30 nmol/L ROX reference dye, and 5 µL of sample DNA. Nontemplate controls consisting of the reaction master mix, primers, and probe, but no DNA, were included in each assay run. Reaction conditions were set as follows: 1 cycle at 95° C. for 15 min, followed by 40 cycles at 94° C. for 1 min and at 60° C. for 1 min. Thermal cycling, fluorescent data collection, and data analysis were performed using the Stratagene Mx3005P system (Stratagene, La Jolla, Calif.) according to the manufacturer's instructions.

Example 13

Detection of Serum Antibody and Isotype Levels by ELISA

Serum was analyzed by an enzyme-linked immunosorbent assay (ELISA). Nunc™ C96 Maxisorp Immunoplates (Thermo Scientific, Waltham, Mass.) were coated with 50 uL of 1 ug/ml C. trachomatis Serovar D EBs in PBS and refrigerated overnight. The plates were washed three times with 0.05% Tween-20 (Fisher Scientific) in PBS (PBS-T). The wells were blocked with 5% HyClone® Fetal Bovine Serum (FBS) (Thermo Scientific) in PBS at 200 µL/well for 1 hour at room temperature and washed three times with PBS-T. Serum was diluted in 5% FBS in PBS at a 1:500 dilution. Serially diluted sera were added to the plate, incubated for 2 hours at room temperature and the plates were washed three times with PBS-T. HRP-conjugated secondary antibodies (Goat anti-mouse IgG, Fcγ fragment specific; Goat Anti-mouse IgG, Fcγ Subclass 1 specific; or Goat Anti-mouse IgG, Fcγ Subclass 2c specific; Jackson ImmunoResearch Laboratories, Inc., West Grove, Pa.) were diluted in 5% FBS in PBS at 1:6,000, 1:6,000, or 1:2,000 dilution, respectively. The diluted secondary antibodies were added at 100 µL/well, incubated for 1 hour at room temperature and the plates were washed three times with PBS-T followed by three times with PBS. Room temperature BD Opt EIA™ TMB Substrate Reagent Set (BD Biosciences, Franklin Lakes, N.J.) was mixed and filtered through a 0.22 um CA filter unit (Corning, Inc., Corning N.Y.), and 100 µL was added to each well and incubated for 10 min at room temperature. The reaction was stopped with 100 µL/well of 2M $H_2SO_4$ (Fisher Scientific). The optical density (OD) was read at 450 nm on a SpectraMax® M5 (Molecular Devices). The cutoff OD for each post-immunization serum was calculated as two times of the $OD_{450}$ of the corresponding pre-immunization serum. ELISA titers were determined by linearly interpolating between the sequential log dilutions that bracket the cutoff OD, where the dependent variable is the OD response and the independent variable is the log dilution. The resulting dilution is then back transformed to obtain the reported titer. The reported titer is the estimated dilution of serum that results in a response equivalent to the cutoff OD.

What is claimed is:

1. A nucleic acid molecule comprising a sequence of nucleotides as set forth in SEQ ID NO:15, SEQ ID NO:18, or SEQ ID NO:21.

2. The nucleic acid molecule of claim 1, comprising a sequence of nucleotides as set forth in SEQ ID NO:15.

3. The nucleic acid molecule of claim 1, comprising a sequence of nucleotides as set forth in SEQ ID NO:18.

4. The nucleic acid molecule of claim 1, comprising a sequence of nucleotides as set forth in SEQ ID NO:21.

5. A nucleic acid molecule comprising a nucleic acid derivative having at least 85% sequence identity to a sequence of nucleotides set forth in SEQ ID NO 15, SEQ ID NO: 18, or SEQ ID NO: 21, wherein the nucleic acid molecule retains the leader sequence.

6. A nucleic acid molecule comprising a nucleic acid derivative having at least 90% sequence identity to a sequence of nucleotides set forth in SEQ ID NO 15, SEQ ID NO: 18, or SEQ ID NO: 21, wherein the nucleic acid molecule retains the leader sequence.

7. A nucleic acid molecule comprising a nucleic acid derivative having at least 95% sequence identity to a sequence of nucleotides set forth in SEQ ID NO 15, SEQ ID NO: 18, or SEQ ID NO: 21, wherein the nucleic acid molecule retains the leader sequence.

8. A nucleic acid molecule comprising a nucleic acid derivative having at least 97% sequence identity to a sequence of nucleotides set forth in SEQ ID NO 15, SEQ ID NO: 18, or SEQ ID NO: 21, wherein the nucleic acid molecule retains the leader sequence.

9. A nucleic acid molecule comprising a nucleic acid derivative having at least 99% sequence identity to a sequence of nucleotides set forth in SEQ ID NO 15, SEQ ID NO: 18, or SEQ ID NO: 21, wherein the nucleic acid molecule retains the leader sequence.

* * * * *

SEQUENCE LISTING

<160> NUMBER OF SEQ ID NOS: 31

<210> SEQ ID NO 1
<211> LENGTH: 22
<212> TYPE: DNA
<213> ORGANISM: Artificial Sequence
<220> FEATURE:
<223> OTHER INFORMATION: PCR Primer

<400> SEQUENCE: 1
attctgcatt cactggccga gg                                              22

<210> SEQ ID NO 2
<211> LENGTH: 19
<212> TYPE: DNA
<213> ORGANISM: Artificial Sequence
<220> FEATURE:
<223> OTHER INFORMATION: PCR Primer

<400> SEQUENCE: 2
gctagttatt gctcagcgg                                                  19

<210> SEQ ID NO 3

```
<211> LENGTH: 20
<212> TYPE: DNA
<213> ORGANISM: Artificial Sequence
<220> FEATURE:
<223> OTHER INFORMATION: PCR Primer

<400> SEQUENCE: 3
cgcctgagga gtacactcgc                                                    20

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
ccaacacctc acggcacgag                                                    20

<210> SEQ ID NO 5
<211> LENGTH: 26
<212> TYPE: DNA
<213> ORGANISM: Artificial Sequence
<220> FEATURE:
<223> OTHER INFORMATION: Oligonucleotide probe

<400> SEQUENCE: 5
cacaagcagt ggagcatgtg gtttaa                                             26

<210> SEQ ID NO 6
<211> LENGTH: 22
<212> TYPE: PRT
<213> ORGANISM: Chlamydia muridarum

<400> SEQUENCE: 6

Met Lys Lys Leu Leu Lys Ser Val Leu Ala Phe Ala Val Leu Gly Ser
1               5                   10                  15

Ala Ser Ser Leu His Ala
            20

<210> SEQ ID NO 7
<211> LENGTH: 22
<212> TYPE: PRT
<213> ORGANISM: Chlamydia trachomatis

<400> SEQUENCE: 7

Met Lys Lys Leu Leu Lys Ser Val Leu Val Phe Ala Ala Leu Gly Ser
1               5                   10                  15

Ala Ser Ser Leu Gln Ala
            20

<210> SEQ ID NO 8
<211> LENGTH: 20
<212> TYPE: PRT
<213> ORGANISM: Shigella flexneri

<400> SEQUENCE: 8

Met Lys Ser Lys Phe Leu Val Leu Ala Leu Cys Val Pro Ala Ile Phe
1               5                   10                  15

Thr Thr His Ala
            20

<210> SEQ ID NO 9
<211> LENGTH: 20
```

```
<212> TYPE: PRT
<213> ORGANISM: Salmonella enterica

<400> SEQUENCE: 9

Met Lys Thr His Val Ile Ala Val Met Ile Ile Ala Val Phe Ser Glu
1               5                   10                  15

Ser Val Tyr Ala
            20

<210> SEQ ID NO 10
<211> LENGTH: 20
<212> TYPE: PRT
<213> ORGANISM: Yersinia pestis

<400> SEQUENCE: 10

Met Lys Lys Ser Ser Ile Val Ala Thr Ile Ile Thr Ile Leu Ser Gly
1               5                   10                  15

Ser Ala Asn Ala
            20

<210> SEQ ID NO 11
<211> LENGTH: 23
<212> TYPE: PRT
<213> ORGANISM: Escherichia coli

<400> SEQUENCE: 11

Met Gln Thr Lys Leu Leu Ala Ile Met Leu Ala Ala Pro Val Val Phe
1               5                   10                  15

Ser Ser Gln Glu Ala Ser Ala
            20

<210> SEQ ID NO 12
<211> LENGTH: 21
<212> TYPE: PRT
<213> ORGANISM: Escherichia coli

<400> SEQUENCE: 12

Met Lys Lys Thr Ala Ile Ala Ile Ala Val Ala Leu Ala Gly Phe Ala
1               5                   10                  15

Thr Val Ala Gln Ala
            20

<210> SEQ ID NO 13
<211> LENGTH: 22
<212> TYPE: PRT
<213> ORGANISM: Erwinia carotovora

<400> SEQUENCE: 13

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 14
<211> LENGTH: 1174
<212> TYPE: DNA
<213> ORGANISM: Artificial Sequence
<220> FEATURE:
<223> OTHER INFORMATION: Harmonized  PelBL_Cm_MOMP Sequence (NdeI&XhoI
      sites included)

<400> SEQUENCE: 14
catatgaaat acctgctgcc gaccgctgct gctggtctgc tgctcctcgc tgcccagccg      60
```

| | |
|---|---|
| gcgatggccc ctaccggtag gtaacccggc ggaaccatca ttgatgattg acggtatttt | 120 |
| gtgggaaggg ttcgggggcg atccgtgtga tccgtgtacg acctggtgcg atgctatatc | 180 |
| acttcgcctc ggatactatg gtgacttcgt gtttgatcgc gtgcttaaaa cggacgtaaa | 240 |
| taaacaattc gaaatgggcg ccgcgccgac gggcgatgcc gacttgacca cggccccgac | 300 |
| cccggcctca cgtgagaacc ctgcgtatgg aaagcacatg caggatgccg aaatgttcac | 360 |
| caacgcggct tacatggcgc tgaatatttg ggaccgcttc gatgtatttt gcacgcttgg | 420 |
| cgccacctca ggctatttga aagggaacag cgctgctttt aatctggtgg gctatttgg | 480 |
| ccgtgatgaa accgccgtgg ccgcggacga cataccgaat gtatcactta gccaggcggt | 540 |
| ggtagaactc tacacggaca cggcgttcgc gtggtcagta ggggcgcgtg ccgcgctgtg | 600 |
| ggagtgtggc tgcgccaccc tgggcgcgtc cttccagtat gcgcagagca agccaaaagt | 660 |
| agaggaactg aatgtgctct gcaacgctgc cgaattcacc attaataagc gaaaggcta | 720 |
| cgtgggccag gagtttccgt tgaatattaa agcgggcacg gtgtcagcga cggataccaa | 780 |
| agatgcgtcc atagattacc atgagtggca ggcctcactt gcgcttagct accgtctaaa | 840 |
| catgttcacc ccgtacattg gcgtgaagtg gagccgtgcc tcatttgatg ctgacaccat | 900 |
| acggattgct caaccgaagt tggagactag catcctgaaa atgactacct ggaatccaac | 960 |
| aatcagcggc agcgggatag acgtggatac gaaaataaca gatacgctgc agattgtgtc | 1020 |
| ccttcaactc aataagatga atcccgtaa aagctgtggg ttggccattg cacgacgat | 1080 |
| tgtagatgcg gataaatatg ccgtgaccgt ggagacgcgg cttatcgatg aacgtgccgc | 1140 |
| gcacgtaaac gcgcaattcc gcttctaact cgag | 1174 |

<210> SEQ ID NO 15
<211> LENGTH: 1165
<212> TYPE: DNA
<213> ORGANISM: Artificial Sequence
<220> FEATURE:
<223> OTHER INFORMATION: Harmonized PelBL_Cm_MOMP Sequence

<400> SEQUENCE: 15

| | |
|---|---|
| atgaaatacc tgctgccgac cgctgctgct ggtctgctgc tcctcgctgc ccagccggcg | 60 |
| atggccccta ccggtaggta acccggcgga accatcattg atgattgacg gtattttgtg | 120 |
| ggaagggttc gggggcgatc cgtgtgatcc gtgtacgacc tggtgcgatg ctatatcact | 180 |
| tcgcctcgga tactatggtg acttcgtgtt tgatcgcgtg cttaaaacgg acgtaaataa | 240 |
| acaattcgaa atgggcgccg cgccgacggg cgatgccgac ttgaccacgg ccccgacccc | 300 |
| ggcctcacgt gagaaccctg cgtatggaaa gcacatgcag gatgccgaaa tgttccaccaa | 360 |
| cgcggcttac atgcgctga atatttggga ccgcttcgat gtattttgca cgcttggcgc | 420 |
| cacctcaggc tatttgaaag ggaacagcgc tgcttttaat ctggtgggc tatttggccg | 480 |
| tgatgaaacc gccgtggccg cggacgacat accgaatgta tcacttagcc aggcggtggt | 540 |
| agaactctac acggacacgg cgttcgcgtg gtcagtaggg gcgcgtgccg cgctgtggga | 600 |
| gtgtggctgc gccaccctgg gcgcgtcctt ccagtatgcg cagagcaagc caaaagtaga | 660 |
| ggaactgaat gtgctctgca acgctgccga attcaccatt aataagccga aaggctacgt | 720 |
| gggccaggag tttccgttga atattaaagc gggcacggtg tcagcgacgg ataccaaaga | 780 |
| tgcgtccata gattaccatg agtggcaggc ctcacttgcg cttagctacc gtctaaacat | 840 |
| gttcaccccg tacattggcg tgaagtggag ccgtgcctca tttgatgctg acaccatacg | 900 | gattgctcaa ccgaagttgg agactagcat cctgaaaatg actacctgga atccaacaat    960 cagcggcagc gggatagacg tggatacgaa aataacagat acgctgcaga ttgtgtccct   1020 tcaactcaat aagatgaaat cccgtaaaag ctgtggggttg gccattggca cgacgattgt   1080 agatgcggat aaatatgccg tgaccgtgga gacgcggctt atcgatgaac gtgccgcgca   1140 cgtaaacgcg caattccgct tctaa                                          1165

<210> SEQ ID NO 16
<211> LENGTH: 387
<212> TYPE: PRT
<213> ORGANISM: Artificial Sequence
<220> FEATURE:
<223> OTHER INFORMATION: PelB + Cm MOMP
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid

<400> SEQUENCE: 16

Met Lys Tyr Leu Leu Pro Thr Ala Ala Ala Gly Leu Leu Leu Leu Ala
1               5                   10                  15

Ala Gln Pro Ala Met Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Leu Arg Leu Gly Tyr
        50                  55                  60

Tyr Gly Asp Phe Val Phe Asp Arg Val Leu Lys Thr Asp Val Asn Lys
65                  70                  75                  80

Gln Phe Glu Met Gly Ala Ala Pro Thr Gly Asp Ala Asp Leu Thr Thr
                85                  90                  95

Ala Pro Thr Pro Ala Ser Arg Glu Asn Pro Ala Tyr Gly Lys His Met
            100                 105                 110

Gln Asp Ala Glu Met Phe Thr Asn Ala Ala Tyr Met Ala Leu Asn Ile
        115                 120                 125

Trp Asp Arg Phe Asp Val Phe Cys Thr Leu Gly Ala Thr Ser Gly Tyr
130                 135                 140

Leu Lys Gly Asn Ser Ala Ala Phe Asn Leu Val Gly Leu Phe Gly Arg
145                 150                 155                 160

Asp Glu Thr Ala Val Ala Ala Asp Ile Pro Asn Val Ser Leu Ser
                165                 170                 175

Gln Ala Val Val Glu Leu Tyr Thr Asp Thr Ala Phe Ala Trp Ser Val
            180                 185                 190

Gly Ala Arg Ala Ala Leu Trp Glu Cys Gly Cys Ala Thr Leu Gly Ala
        195                 200                 205

Ser Phe Gln Tyr Ala Gln Ser Lys Pro Lys Val Glu Glu Leu Asn Val
    210                 215                 220

Leu Cys Asn Ala Ala Glu Phe Thr Ile Asn Lys Pro Lys Gly Tyr Val
225                 230                 235                 240

Gly Gln Glu Phe Pro Leu Asn Ile Lys Ala Gly Thr Val Ser Ala Thr
                245                 250                 255

Asp Thr Lys Asp Ala Ser Ile Asp Tyr His Glu Trp Gln Ala Ser Leu
            260                 265                 270

```
Ala Leu Ser Tyr Arg Leu Asn Met Phe Thr Pro Tyr Ile Gly Val Lys
            275                 280                 285

Trp Ser Arg Ala Ser Phe Asp Ala Asp Thr Ile Arg Ile Ala Gln Pro
        290                 295                 300

Xaa Leu Glu Thr Ser Ile Leu Xaa Met Thr Thr Trp Asn Pro Thr Ile
305                 310                 315                 320

Ser Gly Ser Gly Ile Asp Val Asp Thr Lys Ile Thr Asp Thr Leu Gln
            325                 330                 335

Ile Val Ser Leu Gln Leu Asn Lys Met Lys Ser Arg Lys Ser Cys Gly
            340                 345                 350

Leu Ala Ile Gly Thr Thr Ile Val Asp Ala Asp Lys Tyr Ala Val Thr
            355                 360                 365

Val Glu Thr Arg Leu Ile Asp Glu Arg Ala Ala His Val Asn Ala Gln
        370                 375                 380

Phe Arg Phe
385

<210> SEQ ID NO 17
<211> LENGTH: 1191
<212> TYPE: DNA
<213> ORGANISM: Artificial Sequence
<220> FEATURE:
<223> OTHER INFORMATION: Harmonized PelBL_CtD_CT_MOMP Sequence(NdeI&XhoI
      sites included)

<400> SEQUENCE: 17
catatgaaat acctgctgcc gaccgctgct gctggtctgc tgctcctcgc tgcccagccg      60
gcgatggccc taccggtcgg gaacccggcg gaaccatcat tgatgatcga cggcattcta     120
tgggaagggt tcggaggcga tccgtgtgat ccgtgtgcta cgtggtgcga cgcgatctca     180
atgcgtgtgg ggtactacgg cgactttgtg ttcgaccgtg tgttgaaaac ggatgtcaac     240
aaagaatttc aaatggggc taagccgacg acggatacgg aaactcagc cgcgccatcc      300 acgttgacgg cccgtgagaa cccggcgtac ggacgtcaca tgcaagatgc ggagatgttt     360
acgaacgctg cgtgtatggc cttgaacatt tgggatcgtt ttgatgtatt ctgcacgctg     420
ggcgctactt caggctatt gaaaggcaat agcgcgagct caacctggt gggcttgttt      480 ggcgataacg aaaccagaa acagtaaaa gctgagagcg taccaaacat gtcatttgat       540
cagagcgtgg tggagttgta tacggatacg acgtttgctt ggtcagtagg agcgcgggcc     600
gcgttgtggg aatgcggctg cgccacgctg ggcgcgtcat tccagtatgc gcagagcaaa     660
ccgaaagtag aagaactgaa tgtgcttgt aacgccgccg agtttacgat taacaaaccg      720
aaagggtatg tagggaagga gtttccgttg gatttgacgg ccggcacgga tgcggctacg     780
ggcacgaagg atgctagcat tgattaccat gaatggcagg cctcactggc gcttagctac     840
cgtctaaaca tgttcacgcc ctacattggc gtgaaatgga gccgtgcctc atttgatgct     900
gatacaattc gtatagctca accaaaatca gcgacgcga ttttgatac gactacattg       960 aatccaacga ttgcgggcgc gggagatgtc aaaacgggag ccgagggca acttggcgac     1020 acgatgcaga tcgtgtccct tgcagttgaa aagatgaaaa gccgtaaaag ctgtgggatt     1080
gccgtaggca cgacgattgt cgatgccgac aaatacgccg tgacggtgga gacgcggttg     1140
atcgatgagc gtgccgcgca cgtaaacgcc cagtaccagt tctaactcga g             1191

<210> SEQ ID NO 18
<211> LENGTH: 1182
<212> TYPE: DNA
```

<213> ORGANISM: Artificial Sequence
<220> FEATURE:
<223> OTHER INFORMATION: Harmonized PelBL_CtD_CT_MOMP Sequence

<400> SEQUENCE: 18

```
atgaaatacc tgctgccgac cgctgctgct ggtct

Ile Trp Asp Arg Phe Asp Val Phe Cys Thr Leu Gly Ala Thr Ser Gly
130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
            165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
            195                 200                 205

Leu Gly Ala Ser Phe Gln Tyr Ala Gln Ser Lys Pro Lys Val Glu Glu
210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
            275                 280                 285

Gly Val Lys Trp Ser Arg Ala Ser Phe Asp Ala Asp Thr Ile Arg Ile
290                 295                 300

Ala Gln Pro Lys Ser Ala Thr Ala Ile Phe Asp Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
            355                 360                 365

Asp Lys Tyr Ala Val Thr Val Glu Thr Arg Leu Ile Asp Glu Arg Ala
        370                 375                 380

Ala His Val Asn Ala Gln Tyr Gln Phe
385                 390

<210> SEQ ID NO 20
<211> LENGTH: 1192
<212> TYPE: DNA
<213> ORGANISM: Artificial Sequence
<220> FEATURE:
<223> OTHER INFORMATION: Harmonized PelBL_CtE_MOMP DNA Sequence
      (NdeI&XhoI sites included)

<400> SEQUENCE: 20
catatgaaat acctgctgcc gaccgctgct gctggtctgc tgctcctcgc tgcccagccg    60
gcgatggccc ctaccggtcg ggaacccggc ggaaccatca ttgatgatcg acggcattct   120
atgggaaggg ttcggaggcg atccgtgtga tccgtgtact acgtggtgcg acgcgatctc   180
aatgcgtatg gggtactatg gggactttgt gttcgaccgt gtgttgaaaa cggatgtcaa   240
caaagaattc cagatggggg acaagccgac gtcaacgacg ggaaacgcga cggcgccaac   300
tacgttgacg gcccgtgaga acccggcgta cggacgtcac atgcaagatg cggagatgtt   360
tacgaacgcc gcgtgtatgg ccttgaacat ttgggatcgg tttgatgtat tctgcacgtt   420
aggcgccagc tcaggctact tgaaaggcaa tagcgcgagc ttcaacctgg tgggcttgtt   480

-continued

| | |
|---|---|
| tggcgataac gaaaaccagt caacagtaaa acaaacagc gtaccaaaca tgtcactgga | 540 |
| tcagagcgtg gtggaattgt acacggatac ggccttcagc tggtcagtcg agcgcgtgc | 600 |
| cgcgttgtgg gagtgtggct gcgctacgct gggggcgagc ttccagtacg cgcagagcaa | 660 |
| accgaaagta aagaactga atgtgctttg caatgccgcg gagtttacga tcaacaagcc | 720 |
| gaaaggctat gtagggcagg aattcccgtt ggcccttata gccggcacgg atgccgctac | 780 |
| aggaacgaaa gatgccagca ttgattacca tgagtggcag gcctcactgg cgcttagcta | 840 |
| ccgtttgaac atgttcacgc cctacattgg cgtgaaatgg agccgtgcct catttgatgc | 900 |
| cgatacaatt cgtatagccc aaccaaaatc agcgacggcg atctttgata cgactacatt | 960 |
| gaatccaacg attgcgggcg cgggagatgt caaagcgtca gccgaggggc aacttggcga | 1020 |
| tactatgcag atcgtatcct tgcagttgaa taagatgaaa agccgtaaaa gctgtgggat | 1080 |
| tgccgtaggc acaacgattg tagatgccga caaatacgcc gtgacggtgg agacgcggtt | 1140 |
| gatcgatgag cgtgcggcgc acgtaaacgc ccagttccgg ttctaactcg ag | 1192 |

<210> SEQ ID NO 21
<211> LENGTH: 1183
<212> TYPE: DNA
<213> ORGANISM: Artificial Sequence
<220> FEATURE:
<223> OTHER INFORMATION: Harmonized PelBL_CtE_MOMP DNA Sequence

<400> SEQUENCE: 21

| | |
|---|---|
| atgaaatacc tgctgccgac cgctgctgct ggtctgctgc tcctcgctgc ccagccggcg | 60 |
| atggcccta ccggtcggga acccggcgga accatcattg atgatcgacg gcattctatg | 120 |
| ggaagggttc ggaggcgatc cgtgtgatcc gtgtactacg tggtgcgacg cgatctcaat | 180 |
| gcgtatgggg tactatgggg actttgtgtt cgaccgtgtg ttgaaaacgg atgtcaacaa | 240 |
| agaattccag atgggggaca agccgacgtc aacgacggga aacgcgacgg cgccaactac | 300 |
| gttgacggcc cgtgagaacc cggcgtacgg acgtcacatg caagatgcgg agatgtttac | 360 |
| gaacgccgcg tgtatggcct tgaacatttg ggatcggttt gatgtattct gcacgttagg | 420 |
| cgccagctca ggctacttga aaggcaatag cgcgagcttc aacctggtgg gcttgtttgg | 480 |
| cgataacgaa aaccagtcaa cagtaaaaac aaacagcgta ccaaacatgt cactggatca | 540 |
| gagcgtggtg gaattgtaca cggatacggc cttcagctgg tcagtcggag cgcgtgccgc | 600 |
| gttgtgggag tgtggctgcg ctacgctggg ggcgagcttc cagtacgcgc agagcaaacc | 660 |
| gaaagtagaa gaactgaatg tgcttttgcaa tgccgcggag tttacgatca acaagccgaa | 720 |
| aggctatgta gggcaggaat cccgttggc ccttatagcc ggcacggatg ccgctacagg | 780 |
| aacgaaagat gccagcattg attaccatga gtggcaggcc tcactggcgc ttagctaccg | 840 |
| tttgaacatg ttcacgccct acattggcgt gaaatggagc cgtgcctcat ttgatgccga | 900 |
| tacaattcgt atagcccaac caaaatcagc gacggcgatc tttgatacga ctacattgaa | 960 |
| tccaacgatt gcgggcgcgg agatgtcaa agcgtcagcc gaggggcaac ttggcgatac | 1020 |
| tatgcagatc gtatccttgc agttgaataa gatgaaaagc cgtaaaagct gtgggattgc | 1080 |
| cgtaggcaca acgattgtag atgccgacaa atacgccgtg acggtggaga cgcggttgat | 1140 |
| cgatgagcgt gcggcgcacg taaacgccca gttccggttc taa | 1183 |

<210> SEQ ID NO 22
<211> LENGTH: 393
<212> TYPE: PRT
<213> ORGANISM: Artificial Sequence
<220> FEATURE:
<223> OTHER INFORMATION: PelBL_CtE_MOMP

<400> SEQUENCE: 22

Met Lys Tyr Leu Leu Pro Thr Ala Ala Ala Gly Leu Leu Leu Ala
1               5                   10                  15

Ala Gln Pro Ala Met Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Asp Lys Pro Thr Ser Thr Thr Gly Asn Ala Thr
            85                  90                  95

Ala Pro Thr Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
            115                 120                 125

Ile Trp Asp Arg Phe Asp Val Phe Cys Thr Leu Gly Ala Ser Ser Gly
        130                 135                 140

Tyr Leu Lys Gly Asn Ser Ala Ser Phe Asn Leu Val Gly Leu Phe Gly
145                 150                 155                 160

Asp Asn Glu Asn Gln Ser Thr Val Lys Thr Asn Ser Val Pro Asn Met
            165                 170                 175

Ser Leu Asp Gln Ser Val Val Glu Leu Tyr Thr Asp Thr Ala Phe Ser
            180                 185                 190

Trp Ser Val Gly Ala Arg Ala Ala Leu Trp Glu Cys Gly Cys Ala Thr
            195                 200                 205

Leu Gly Ala Ser Phe Gln Tyr Ala Gln Ser Lys Pro Lys Val Glu Glu
        210                 215                 220

Leu Asn Val Leu Cys Asn Ala Ala Glu Phe Thr Ile Asn Lys Pro Lys
225                 230                 235                 240

Gly Tyr Val Gly Gln Glu Phe Pro Leu Ala Leu Ile Ala Gly Thr Asp
            245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Ala Ser Ala Glu Gly Gln
            325                 330                 335

Leu Gly Asp Thr Met Gln Ile Val Ser Leu Gln Leu Asn Lys Met Lys
        340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
        370                 375                 380

Ala His Val Asn Ala Gln Phe Arg Phe
385                 390

```
<210> SEQ ID NO 23
<211> LENGTH: 371
<212> TYPE: PRT
<213> ORGANISM: Chlamydia trachomatis

<400> SEQUENCE: 23

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Gln Met Gly Asp
    50                  55                  60

Lys Pro Thr Ser Thr Thr Gly Asn Ala Thr Ala Pro Thr Thr Leu Thr
65                  70                  75                  80

Ala Arg Glu Asn Pro Ala Tyr Gly Arg His Met Gln Asp Ala Glu Met
                85                  90                  95

Phe Thr Asn Ala Ala Cys Met Ala Leu Asn Ile Trp Asp Arg Phe Asp
            100                 105                 110

Val Phe Cys Thr Leu Gly Ala Ser Ser Gly Tyr Leu Lys Gly Asn Ser
        115                 120                 125

Ala Ser Phe Asn Leu Val Gly Leu Phe Gly Asp Asn Glu Asn Gln Ser
    130                 135                 140

Thr Val Lys Thr Asn Ser Val Pro Asn Met Ser Leu Asp Gln Ser Val
145                 150                 155                 160

Val Glu Leu Tyr Thr Asp Thr Ala Phe Ser Trp Ser Val Gly Ala Arg
                165                 170                 175

Ala Ala Leu Trp Glu Cys Gly Cys Ala Thr Leu Gly Ala Ser Phe Gln
            180                 185                 190

Tyr Ala Gln Ser Lys Pro Lys Val Glu Glu Leu Asn Val Leu Cys Asn
        195                 200                 205

Ala Ala Glu Phe Thr Ile Asn Lys Pro Lys Gly Tyr Val Gly Gln Glu
    210                 215                 220

Phe Pro Leu Ala Leu Ile Ala Gly Thr Asp Ala Ala Thr Gly Thr Lys
225                 230                 235                 240

Asp Ala Ser Ile Asp Tyr His Glu Trp Gln Ala Ser Leu Ala Leu Ser
                245                 250                 255

Tyr Arg Leu Asn Met Phe Thr Pro Tyr Ile Gly Val Lys Trp Ser Arg
            260                 265                 270

Ala Ser Phe Asp Ala Asp Thr Ile Arg Ile Ala Gln Pro Lys Ser Ala
        275                 280                 285

Thr Ala Ile Phe Asp Thr Thr Thr Leu Asn Pro Thr Ile Ala Gly Ala
    290                 295                 300

Gly Asp Val Lys Ala Ser Ala Glu Gly Gln Leu Gly Asp Thr Met Gln
305                 310                 315                 320

Ile Val Ser Leu Gln Leu Asn Lys Met Lys Ser Arg Lys Ser Cys Gly
                325                 330                 335

Ile Ala Val Gly Thr Thr Ile Val Asp Ala Asp Lys Tyr Ala Val Thr
            340                 345                 350

Val Glu Thr Arg Leu Ile Asp Glu Arg Ala Ala His Val Asn Ala Gln
        355                 360                 365

Phe Arg Phe
```

370

<210> SEQ ID NO 24
<211> LENGTH: 371
<212> TYPE: PRT
<213> ORGANISM: Artificial Sequence
<220> FEATURE:
<223> OTHER INFORMATION: C. trachomatis, serovar D with Bam modification

<400> SEQUENCE: 24

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Ala Thr Trp
            20                  25                  30

Cys Asp Ala Ile Ser Met Arg Val Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Lys Pro Thr Thr Asp Thr Gly Asn Ser Ala Ala Pro Ser Thr Leu Thr
65                  70                  75                  80

Ala Arg Glu Asn Pro Ala Tyr Gly Arg His Met Gln Asp Ala Glu Met
                85                  90                  95

Phe Thr Asn Ala Ala Cys Met Ala Leu Asn Ile Trp Asp Arg Phe Asp
            100                 105                 110

Val Phe Cys Thr Leu Gly Ala Thr Ser Gly Tyr Leu Lys Gly Asn Ser
        115                 120                 125

Ala Ser Phe Asn Leu Val Gly Leu Phe Gly Asp Asn Glu Asn Gln Lys
    130                 135                 140

Thr Val Lys Ala Glu Ser Val Pro Asn Met Ser Phe Asp Gln Ser Val
145                 150                 155                 160

Val Glu Leu Tyr Thr Asp Thr Thr Phe Ala Trp Ser Val Gly Ala Arg
                165                 170                 175

Ala Ala Leu Trp Glu Cys Gly Cys Ala Thr Leu Gly Ala Ser Phe Gln
            180                 185                 190

Tyr Ala Gln Ser Lys Pro Lys Val Glu Glu Leu Asn Val Leu Cys Asn
        195                 200                 205

Ala Ala Glu Phe Thr Ile Asn Lys Pro Lys Gly Tyr Val Gly Lys Glu
    210                 215                 220

Phe Pro Leu Asp Leu Thr Ala Gly Thr Asp Ala Ala Thr Gly Thr Lys
225                 230                 235                 240

Asp Ala Ser Ile Asp Tyr His Glu Trp Gln Ala Ser Leu Ala Leu Ser
                245                 250                 255

Tyr Arg Leu Asn Met Phe Thr Pro Tyr Ile Gly Val Lys Trp Ser Arg
            260                 265                 270

Ala Ser Phe Asp Ala Asp Thr Ile Arg Ile Ala Gln Pro Lys Ser Ala
        275                 280                 285

Thr Ala Ile Phe Asp Thr Thr Leu Asn Pro Thr Ile Ala Gly Ala
    290                 295                 300

Gly Asp Val Lys Thr Gly Ala Glu Gly Gln Leu Gly Asp Thr Met Gln
305                 310                 315                 320

Ile Val Ser Leu Gln Leu Asn Lys Met Lys Ser Arg Lys Ser Cys Gly
                325                 330                 335

Ile Ala Val Gly Thr Thr Ile Val Asp Ala Asp Lys Tyr Ala Val Thr
            340                 345                 350

Val Glu Thr Arg Leu Ile Asp Glu Arg Ala Ala His Val Asn Ala Gln

```
              355                 360                 365

Tyr Gln Phe
        370

<210> SEQ ID NO 25
<211> LENGTH: 371
<212> TYPE: PRT
<213> ORGANISM: Chlamydia trachomatis

<400> SEQUENCE: 25

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Ala Thr Trp
            20                  25                  30

Cys Asp Ala Ile Ser Met Arg Val Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Lys Pro Thr Thr Asp Thr Gly Asn Ser Ala Ala Pro Ser Thr Leu Thr
65                  70                  75                  80

Ala Arg Glu Asn Pro Ala Tyr Gly Arg His Met Gln Asp Ala Glu Met
                85                  90                  95

Phe Thr Asn Ala Ala Cys Met Ala Leu Asn Ile Trp Asp Arg Phe Asp
            100                 105                 110

Val Phe Cys Thr Leu Gly Ala Thr Ser Gly Tyr Leu Lys Gly Asn Ser
        115                 120                 125

Ala Ser Phe Asn Leu Val Gly Leu Phe Gly Asp Asn Glu Asn Gln Lys
    130                 135                 140

Thr Val Lys Ala Glu Ser Val Pro Asn Met Ser Phe Asp Gln Ser Val
145                 150                 155                 160

Val Glu Leu Tyr Thr Asp Thr Thr Phe Ala Trp Ser Val Gly Ala Arg
                165                 170                 175

Ala Ala Leu Trp Glu Cys Gly Cys Ala Thr Leu Gly Ala Ser Phe Gln
            180                 185                 190

Tyr Ala Gln Ser Lys Pro Lys Val Glu Glu Leu Asn Val Leu Cys Asn
        195                 200                 205

Ala Ala Glu Phe Thr Ile Asn Lys Pro Lys Gly Tyr Val Gly Lys Glu
    210                 215                 220

Phe Pro Leu Asp Leu Thr Ala Gly Thr Asp Ala Ala Thr Gly Thr Lys
225                 230                 235                 240

Asp Ala Ser Ile Asp Tyr His Glu Trp Gln Ala Ser Leu Ala Leu Ser
                245                 250                 255

Tyr Arg Leu Asn Met Phe Thr Pro Tyr Ile Gly Val Lys Trp Ser Arg
            260                 265                 270

Ala Ser Phe Asp Ala Asp Thr Ile Arg Ile Ala Gln Pro Lys Ser Ala
        275                 280                 285

Thr Ala Ile Phe Asp Thr Thr Thr Leu Asn Pro Thr Ile Ala Gly Ala
    290                 295                 300

Gly Asp Val Lys Thr Gly Ala Glu Gly Gln Leu Gly Asp Thr Met Gln
305                 310                 315                 320

Ile Val Ser Leu Gln Leu Asn Lys Met Lys Ser Arg Lys Ser Cys Gly
                325                 330                 335

Ile Ala Val Gly Thr Thr Ile Val Asp Ala Asp Lys Tyr Ala Val Thr
            340                 345                 350
```

Val Glu Thr Arg Leu Ile Asp Glu Arg Ala Ala His Val Asn Ala Gln
        355                 360                 365

Phe Arg Phe
    370

<210> SEQ ID NO 26
<211> LENGTH: 373
<212> TYPE: PRT
<213> ORGANISM: Chlamydia trachomatis

<400> SEQUENCE: 26

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Glu Met Gly Glu
    50                  55                  60

Ala Leu Ala Gly Ala Ser Gly Asn Thr Thr Ser Thr Leu Ser Lys Leu
65                  70                  75                  80

Val Glu Arg Thr Asn Pro Ala Tyr Gly Lys His Met Gln Asp Ala Glu
                85                  90                  95

Met Phe Thr Asn Ala Ala Cys Met Ala Leu Asn Ile Trp Asp Arg Phe
            100                 105                 110

Asp Val Phe Cys Thr Leu Gly Ala Thr Ser Gly Tyr Leu Arg Gly Asn
        115                 120                 125

Ser Ala Ser Phe Asn Leu Val Gly Leu Phe Gly Asp Ser Glu Asn Ala
    130                 135                 140

Thr Gln Pro Ala Ala Thr Ser Ile Pro Asn Val Gln Leu Asn Gln Ser
145                 150                 155                 160

Val Val Glu Leu Tyr Thr Asp Thr Ala Phe Ala Trp Ser Val Gly Ala
                165                 170                 175

Arg Ala Ala Leu Trp Glu Cys Gly Cys Ala Thr Leu Gly Ala Ser Phe
            180                 185                 190

Gln Tyr Ala Gln Ser Lys Pro Lys Val Glu Glu Leu Asn Val Leu Cys
        195                 200                 205

Asn Ala Ala Glu Phe Thr Ile Asn Lys Pro Lys Gly Tyr Val Gly Gln
    210                 215                 220

Glu Phe Pro Leu Ala Leu Thr Ala Gly Thr Asp Ala Ala Thr Gly Thr
225                 230                 235                 240

Lys Asp Ala Ser Ile Asp Tyr His Glu Trp Gln Ala Ser Leu Ser Leu
                245                 250                 255

Ser Tyr Arg Leu Asn Met Phe Thr Pro Tyr Ile Gly Val Lys Trp Ser
            260                 265                 270

Arg Ala Ser Phe Asp Ser Asn Thr Ile Arg Ile Ala Gln Pro Lys Leu
        275                 280                 285

Ala Lys Pro Val Val Asp Ile Thr Thr Leu Asn Pro Thr Ile Ala Gly
    290                 295                 300

Cys Gly Ser Val Val Ala Ala Asn Ser Glu Gly Gln Ile Ser Asp Thr
305                 310                 315                 320

Met Gln Ile Val Ser Leu Gln Leu Asn Lys Met Lys Ser Arg Lys Ser
                325                 330                 335

Cys Gly Ile Ala Val Gly Thr Thr Ile Val Asp Ala Asp Lys Tyr Ala
            340                 345                 350

Val Thr Val Glu Thr Arg Leu Ile Asp Glu Arg Ala Ala His Val Asn
            355                 360                 365

Ala Gln Phe Arg Phe
        370

<210> SEQ ID NO 27
<211> LENGTH: 373
<212> TYPE: PRT
<213> ORGANISM: Chlamydia trachomatis

<400> SEQUENCE: 27

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Glu Met Gly Glu
    50                  55                  60

Ala Leu Ala Gly Ala Ser Gly Asn Thr Thr Ser Thr Leu Ser Lys Leu
65                  70                  75                  80

Val Glu Arg Thr Asn Pro Ala Tyr Gly Lys His Met Gln Asp Ala Glu
                85                  90                  95

Met Phe Thr Asn Ala Ala Cys Met Thr Leu Asn Ile Trp Asp Arg Phe
            100                 105                 110

Asp Val Phe Cys Thr Leu Gly Ala Thr Ser Gly Tyr Leu Lys Gly Asn
        115                 120                 125

Ser Ala Ser Phe Asn Leu Val Gly Leu Phe Gly Asp Gly Val Asn Ala
    130                 135                 140

Thr Lys Pro Ala Ala Asp Ser Ile Pro Asn Val Gln Leu Asn Gln Ser
145                 150                 155                 160

Val Val Glu Leu Tyr Thr Asp Thr Thr Phe Ala Trp Ser Val Gly Ala
                165                 170                 175

Arg Ala Ala Leu Trp Glu Cys Gly Cys Ala Thr Leu Gly Ala Ser Phe
            180                 185                 190

Gln Tyr Ala Gln Ser Lys Pro Lys Ile Glu Glu Leu Asn Val Leu Cys
        195                 200                 205

Asn Ala Ala Glu Phe Thr Ile Asn Lys Pro Lys Gly Tyr Val Gly Lys
    210                 215                 220

Glu Phe Pro Leu Asp Leu Thr Ala Gly Thr Asp Ala Ala Thr Gly Thr
225                 230                 235                 240

Lys Asp Ala Ser Ile Asp Tyr His Glu Trp Gln Ala Ser Leu Ser Leu
                245                 250                 255

Ser Tyr Arg Leu Asn Met Phe Thr Pro Tyr Ile Gly Val Lys Trp Ser
            260                 265                 270

Arg Ala Ser Phe Asp Ser Asp Thr Ile Arg Ile Ala Gln Pro Arg Leu
        275                 280                 285

Val Thr Pro Val Val Asp Ile Thr Thr Leu Asn Pro Thr Ile Ala Gly
    290                 295                 300

Cys Gly Ser Val Ala Gly Ala Asn Thr Glu Gly Gln Ile Ser Asp Thr
305                 310                 315                 320

Met Gln Ile Val Ser Leu Gln Leu Asn Lys Met Lys Ser Arg Lys Ser
                325                 330                 335

Cys Gly Ile Ala Val Gly Thr Thr Ile Val Asp Ala Asp Lys Tyr Ala

```
                    340                 345                 350
Val Thr Val Glu Thr Arg Leu Ile Asp Glu Arg Ala Ala His Val Asn
                355                 360                 365

Ala Gln Phe Arg Phe
        370

<210> SEQ ID NO 28
<211> LENGTH: 375
<212> TYPE: PRT
<213> ORGANISM: Chlamydia trachomatis

<400> SEQUENCE: 28

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Ala Pro Thr Thr Lys Asp Ile Ala Gly Leu Glu Asn Asp Pro Thr Thr
65                  70                  75                  80

Asn Val Ala Arg Pro Asn Pro Ala Tyr Gly Lys His Met Gln Asp Ala
                85                  90                  95

Glu Met Phe Thr Asn Ala Ala Tyr Met Ala Leu Asn Ile Trp Asp Arg
            100                 105                 110

Phe Asp Val Phe Cys Thr Leu Gly Ala Thr Thr Gly Tyr Leu Lys Gly
        115                 120                 125

Asn Ser Ala Ser Phe Asn Leu Val Gly Leu Phe Gly Thr Lys Thr Gln
    130                 135                 140

Ser Ser Asn Phe Asn Thr Ala Lys Leu Ile Pro Asn Ala Ala Leu Asn
145                 150                 155                 160

Gln Ala Val Val Glu Leu Tyr Thr Asp Thr Thr Phe Ala Trp Ser Val
                165                 170                 175

Gly Ala Arg Ala Ala Leu Trp Glu Cys Gly Cys Ala Thr Leu Gly Ala
            180                 185                 190

Ser Phe Gln Tyr Ala Gln Ser Lys Pro Lys Val Glu Glu Leu Asn Val
        195                 200                 205

Leu Cys Asn Ala Ser Glu Phe Thr Ile Asn Lys Pro Lys Gly Tyr Val
    210                 215                 220

Gly Ala Glu Phe Pro Leu Asp Ile Thr Ala Gly Thr Glu Ala Ala Thr
225                 230                 235                 240

Gly Thr Lys Asp Ala Ser Ile Asp Tyr His Glu Trp Gln Ala Ser Leu
                245                 250                 255

Ala Leu Ser Tyr Arg Leu Asn Met Phe Thr Pro Tyr Ile Gly Val Lys
            260                 265                 270

Trp Ser Arg Val Ser Phe Asp Ala Asp Thr Ile Arg Ile Ala Gln Pro
        275                 280                 285

Lys Leu Ala Glu Ala Ile Leu Asp Val Thr Thr Leu Asn Pro Thr Ile
    290                 295                 300

Ala Gly Lys Gly Thr Val Val Ala Ser Gly Ser Asp Asn Asp Leu Ala
305                 310                 315                 320

Asp Thr Met Gln Ile Val Ser Leu Gln Leu Asn Lys Met Lys Ser Arg
                325                 330                 335
```

Lys Ser Cys Gly Ile Ala Val Gly Thr Thr Ile Val Asp Ala Asp Lys
                340                 345                 350

Tyr Ala Val Thr Val Glu Thr Arg Leu Ile Asp Glu Arg Ala Ala His
            355                 360                 365

Val Asn Ala Gln Phe Arg Phe
        370                 375

<210> SEQ ID NO 29
<211> LENGTH: 375
<212> TYPE: PRT
<213> ORGANISM: Chlamydia trachomatis

<400> SEQUENCE: 29

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Ala Pro Thr Thr Ser Asp Val Ala Gly Leu Gln Asn Asp Pro Thr Thr
65                  70                  75                  80

Asn Val Ala Arg Pro Asn Pro Ala Tyr Gly Lys His Met Gln Asp Ala
                85                  90                  95

Glu Met Phe Thr Asn Ala Ala Tyr Met Ala Leu Asn Ile Trp Asp Arg
            100                 105                 110

Phe Asp Val Phe Cys Thr Leu Gly Ala Thr Thr Gly Tyr Leu Lys Gly
        115                 120                 125

Asn Ser Ala Ser Phe Asn Leu Val Gly Leu Phe Gly Thr Lys Thr Gln
    130                 135                 140

Ala Ser Ser Phe Asn Thr Ala Asn Leu Phe Pro Asn Thr Ala Leu Asn
145                 150                 155                 160

Gln Ala Val Val Glu Leu Tyr Thr Asp Thr Thr Phe Ala Trp Ser Val
                165                 170                 175

Gly Ala Arg Ala Ala Leu Trp Glu Cys Gly Cys Ala Thr Leu Gly Ala
            180                 185                 190

Ser Phe Gln Tyr Ala Gln Ser Lys Pro Lys Val Glu Glu Leu Asn Val
        195                 200                 205

Leu Cys Asn Ala Ser Glu Phe Thr Ile Asn Lys Pro Lys Gly Tyr Val
    210                 215                 220

Gly Ala Glu Phe Pro Leu Asp Ile Thr Ala Gly Thr Glu Ala Ala Thr
225                 230                 235                 240

Gly Thr Lys Asp Ala Ser Ile Asp Tyr His Glu Trp Gln Ala Ser Leu
                245                 250                 255

Ala Leu Ser Tyr Arg Leu Asn Met Phe Thr Pro Tyr Ile Gly Val Lys
            260                 265                 270

Trp Ser Arg Val Ser Phe Asp Ala Asp Thr Ile Arg Ile Ala Gln Pro
        275                 280                 285

Lys Leu Ala Glu Ala Ile Leu Asp Val Thr Thr Leu Asn Pro Thr Ile
    290                 295                 300

Ala Gly Lys Gly Thr Val Val Ala Ser Gly Ser Glu Asn Asp Leu Ala
305                 310                 315                 320

Asp Thr Met Gln Ile Val Ser Leu Gln Leu Asn Lys Met Lys Ser Arg
                325                 330                 335

```
Lys Ser Cys Gly Ile Ala Val Gly Thr Thr Ile Val Asp Ala Asp Lys
            340                 345                 350

Tyr Ala Val Thr Val Glu Thr Arg Leu Ile Asp Glu Arg Ala Ala His
            355                 360                 365

Val Asn Ala Gln Phe Arg Phe
            370             375

<210> SEQ ID NO 30
<211> LENGTH: 375
<212> TYPE: PRT
<213> ORGANISM: Chlamydia trachomatis

<400> SEQUENCE: 30

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Ala Thr Trp
            20                  25                  30

Cys Asp Ala Ile Ser Met Arg Val Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Ala Pro Thr Thr Asn Asp Ala Asp Leu Gln Asn Asp Pro Lys Thr
65              70                  75                  80

Asn Val Ala Arg Pro Asn Pro Ala Tyr Gly Lys His Met Gln Asp Ala
            85                  90                  95

Glu Met Phe Thr Asn Ala Ala Tyr Met Ala Leu Asn Ile Trp Asp Arg
        100                 105                 110

Phe Asp Val Phe Cys Thr Leu Gly Ala Thr Thr Gly Tyr Leu Lys Gly
    115                 120                 125

Asn Ser Ala Ser Phe Asn Leu Val Gly Leu Phe Gly Thr Lys Thr Lys
130                 135                 140

Ser Ser Asp Phe Asn Thr Ala Lys Leu Val Pro Asn Ile Ala Leu Asn
145                 150                 155                 160

Arg Ala Val Val Glu Leu Tyr Thr Asp Thr Thr Phe Ala Trp Ser Val
            165                 170                 175

Gly Ala Arg Ala Ala Leu Trp Glu Cys Gly Cys Ala Thr Leu Gly Ala
        180                 185                 190

Ser Phe Gln Tyr Ala Gln Ser Lys Pro Lys Val Glu Glu Leu Asn Val
    195                 200                 205

Leu Cys Asn Ala Ser Glu Phe Thr Ile Asn Lys Pro Lys Gly Tyr Val
210                 215                 220

Gly Ala Glu Phe Pro Leu Asp Ile Thr Ala Gly Thr Glu Ala Ala Thr
225                 230                 235                 240

Gly Thr Lys Asp Ala Ser Ile Asp Tyr His Glu Trp Gln Ala Ser Leu
            245                 250                 255

Ala Leu Ser Tyr Arg Leu Asn Met Phe Thr Pro Tyr Ile Gly Val Lys
        260                 265                 270

Trp Ser Arg Val Ser Phe Asp Ala Asp Thr Ile Arg Ile Ala Gln Pro
    275                 280                 285

Lys Leu Ala Glu Ala Ile Leu Asp Val Thr Thr Leu Asn Pro Thr Ile
    290                 295                 300

Ala Gly Lys Gly Thr Val Val Ala Ser Gly Ser Asp Asn Asp Leu Ala
305                 310                 315                 320

Asp Thr Met Gln Ile Val Ser Leu Gln Leu Asn Lys Met Lys Ser Arg
```

```
            325                 330                 335
Lys Ser Cys Gly Ile Ala Val Gly Thr Thr Ile Val Asp Ala Asp Lys
        340                 345                 350

Tyr Ala Val Thr Val Glu Thr Arg Leu Ile Asp Glu Arg Ala Ala His
        355                 360                 365

Val Asn Ala Gln Phe Arg Phe
        370                 375

<210> SEQ ID NO 31
<211> LENGTH: 365
<212> TYPE: PRT
<213> ORGANISM: Chlamydia muridarum

<400> SEQUENCE: 31

Leu Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Leu Arg Leu Gly Tyr Tyr Gly Asp Phe Val Phe
        35                  40                  45

Asp Arg Val Leu Lys Thr Asp Val Asn Lys Gln Phe Glu Met Gly Ala
    50                  55                  60

Ala Pro Thr Gly Asp Ala Asp Leu Thr Thr Ala Pro Thr Pro Ala Ser
65                  70                  75                  80

Arg Glu Asn Pro Ala Tyr Gly Lys His Met Gln Asp Ala Glu Met Phe
                85                  90                  95

Thr Asn Ala Ala Tyr Met Ala Leu Asn Ile Trp Asp Arg Phe Asp Val
            100                 105                 110

Phe Cys Thr Leu Gly Ala Thr Ser Gly Tyr Leu Lys Gly Asn Ser Ala
        115                 120                 125

Ala Phe Asn Leu Val Gly Leu Phe Gly Arg Asp Glu Thr Ala Val Ala
    130                 135                 140

Ala Asp Asp Ile Pro Asn Val Ser Leu Ser Gln Ala Val Val Glu Leu
145                 150                 155                 160

Tyr Thr Asp Thr Ala Phe Ala Trp Ser Val Gly Ala Arg Ala Ala Leu
                165                 170                 175

Trp Glu Cys Gly Cys Ala Thr Leu Gly Ala Ser Phe Gln Tyr Ala Gln
            180                 185                 190

Ser Lys Pro Lys Val Glu Glu Leu Asn Val Leu Cys Asn Ala Ala Glu
        195                 200                 205

Phe Thr Ile Asn Lys Pro Lys Gly Tyr Val Gly Gln Glu Phe Pro Leu
    210                 215                 220

Asn Ile Lys Ala Gly Thr Val Ser Ala Thr Asp Thr Lys Asp Ala Ser
225                 230                 235                 240

Ile Asp Tyr His Glu Trp Gln Ala Ser Leu Ala Leu Ser Tyr Arg Leu
                245                 250                 255

Asn Met Phe Thr Pro Tyr Ile Gly Val Lys Trp Ser Arg Ala Ser Phe
            260                 265                 270

Asp Ala Asp Thr Ile Arg Ile Ala Gln Pro Lys Leu Glu Thr Ser Ile
        275                 280                 285

Leu Lys Met Thr Thr Trp Asn Pro Thr Ile Ser Gly Ser Gly Ile Asp
    290                 295                 300

Val Asp Thr Lys Ile Thr Asp Thr Leu Gln Ile Val Ser Leu Gln Leu
305                 310                 315                 320
```

```
Asn Lys Met Lys Ser Arg Lys Ser Cys Gly Leu Ala Ile Gly Thr Thr
                325                 330                 335

Ile Val Asp Ala Asp Lys Tyr Ala Val Thr Val Glu Thr Arg Leu Ile
            340                 345                 350

Asp Glu Arg Ala Ala His Val Asn Ala Gln Phe Arg Phe
        355                 360                 365
```